(12) United States Patent
Kahn et al.

(10) Patent No.: US 7,444,293 B1
(45) Date of Patent: Oct. 28, 2008

(54) PROTOCOL DISAMBIGUATION USING A MODEL-BASED METHODOLOGY

(75) Inventors: Michael G. Kahn, Boulder, CO (US); Carol A. Broverman, Menlo Park, CA (US); Kelly A. Kingdon, San Rafael, CA (US)

(73) Assignee: FastTrack Systems, Inc., San Mateo, CA (US)

( * ) Notice: Subject to any disclaimer, the term of this patent is extended or adjusted under 35 U.S.C. 154(b) by 990 days.

(21) Appl. No.: 09/974,781

(22) Filed: Oct. 10, 2001

Related U.S. Application Data

(63) Continuation-in-part of application No. 09/584,936, filed on May 31, 2000.

(51) Int. Cl.
 *G06Q 50/00* (2006.01)
(52) U.S. Cl. ............................... 705/3; 705/2; 707/100; 707/104.1; 717/135; 600/300; 704/9
(58) Field of Classification Search ..................... 705/2, 705/3; 600/300; 707/104.1, 100; 704/9; 717/235
See application file for complete search history.

(56) References Cited

U.S. PATENT DOCUMENTS

| | | | | |
|---|---|---|---|---|
| 5,812,983 | A * | 9/1998 | Kumagai ........................ | 705/3 |
| 5,812,984 | A * | 9/1998 | Goltra ............................. | 705/3 |
| 5,832,449 | A * | 11/1998 | Cunningham ................... | 705/3 |
| 5,867,821 | A * | 2/1999 | Ballantyne et al. .............. | 705/2 |
| 5,991,731 | A * | 11/1999 | Colon et al. .................... | 705/3 |
| 6,055,494 | A * | 4/2000 | Friedman ........................ | 704/9 |
| 6,081,786 | A * | 6/2000 | Barry et al. ..................... | 705/3 |
| 6,081,809 | A * | 6/2000 | Kumagai ................. | 707/104.1 |
| 6,108,635 | A * | 8/2000 | Herren et al. ................... | 705/2 |
| 6,196,970 | B1 * | 3/2001 | Brown ........................ | 600/300 |
| 7,054,823 | B1 * | 5/2006 | Briegs et al. .................... | 705/2 |
| 2002/0016530 | A1 * | 2/2002 | Brown ........................ | 600/300 |

OTHER PUBLICATIONS

"Decision support for clinical trial eligibility determination in breast cancer"; L Ohno-Machado, SJ Wang, P Mar, AA Boxwala-Proc AMIA Symp, 1999.*

"EON: A component-based approach to automation of protocol-directed therapy"; MA Musen, SW Tu, AK Das, Y Shahar-J Am Med Inform Assoc., 1996.*

(Continued)

*Primary Examiner*—Jeffrey A. Smith
*Assistant Examiner*—Dilek B Cobanoglu
(74) *Attorney, Agent, or Firm*—Warren S. Wolfeld; Haynes Beffel & Wolfeld LLP

(57) ABSTRACT

Structure and methodology for reducing risk of protocol ambiguities that could lead to operational failures in the conduct of clinical trials. Roughly described, an analyst encodes the features of a protocol into a highly structured, formal model created specifically to capture issues that tend to cause operational difficulties. The process forces the analyst to look for specific parameters in the text version of the protocol. The system creates a database of the protocol as encoded, and can display the protocol schema as a graphical network of protocol events and temporal links. In one aspect, the database includes an object class into which an analyst encodes descriptions of operational uncertainties. The system can display the network in graphical-visual form, with a human-perceptible indication of objects that have operational uncertainties associated therewith. Advantageously, the formal protocol model includes slots for encoding temporal constraints among protocol events.

32 Claims, 41 Drawing Sheets

OTHER PUBLICATIONS

"Unitized data system: Anew formalism for encoding and presenting data from the scientific research literature"; DP Fan, JM Curtsinger, L Johnson, S Kalkhar- Journal of the American Society for Information Science, 1992.*

Brown, et al., U.S. Appl. No. 09/974,781, filed Oct. 10, 2001, entitled Leveraging Interaction with a Community of Individuals. 84 pages.

DataEdge LLC. Indexes of Clinical Study Complexity, 1993-1999. In: Mathieu MP, editor. Parexel's Pharmaceutical R&D Statistical Sourcebook 2000. Waltham, MA: Parexel International Corp; 2000. p. 66.

DataEdge LLC. Indexes of Clinical Trial Costs Per Patient, 1993-1999. In: Mathieu MP, editor. Parexel's Pharmaceutical R&D Statistical Sourcebook 2000. Waltham, MA: Parexel International Corp; 2000. p. 67.

Grosso W. E. et al.; "Knowledge Modeling at the Millennium (The Design and Evolution of Protégé-2000)," SMI Report No. SMI-1999-0801 (1999), available at http://smi-web.stanford.edu/ pubs/ SMI_Abstracts/SMI-1999-0801.html, visited Jan. 1, 2000.

Holford N. H. G.; Kimko H. C.; Monteleone J. P. R., and Peck C. C.; "Simulation of Clinical Trials," Annu. Rev. Pharmacol. Toxicol. 2000, 40:209-34, 2000, Annual Reviews.

"ICH Harmonised Tripartite Guideline: General Considerations for Clinical Trials," International Conference on Harmonisation of Technical Requirements for Registration of Pharmaceuticals for Human Use recommended for adoption on Jul. 17, 1997, URL: www.ifpma.org/ich5c.html, Accessed: Aug. 31, 2001.

"ICH Harmonised Tripartite Guideline: Guideline for Good Clinical Practice," International Conference on Harmonisation of Technical Requirements for Registration of Pharmaceuticals for Human Use recommended for adoption on May 1, 1996, URL: www.ifphma.org/ich5e.html, Accessed: Aug. 31, 2001.

Kroll J. A.; De Bruin A.; Getz K.; Eschmann K.; and Zisson S.; "Study Conduct Delays are Getting Worse," In: Kroll JA, editor. An Industry In Evolution. Second ed. Boston, MA: CenterWatch; 1999. p. 99.

Musen M. A.; "Domain Ontologies in Software Engineering: Use of Protégé with the EON Architecture," Methods of Information in Medicine, F.K. Schattauer Verlagsgesellschaft mbH (1998); 37:540-50.

Musen M. A.; Gennari J. H.; Eriksson H.; Tu S. W., and Puerta A. R.; Protégé-II: Computer Support for Development of Intelligent Systems from Libraries of Components, MEDINFO 95 Proceedings, R. A. Greenes et al. (editors); 8(1):766-70.

Musen M.A.; Rohn J. A.; Fagan L. M.; and Shortliffe E. H.; "Knowledge Engineering for a Clinical Trial Advice System: Uncovering Errors in Protocol Specification," Report KSL-85-51, Proceedings AAMSI Congress 1986 (Levy, A.H. and Williams, B.T., eds.), pp. 24-27, Anaheim CA, May 1986.

Sheiner L. B. and Steimer J. L.; "Pharmacokinetic/ Pharmacodynamic Modeling in Drug Development," Annu. Rev. Pharmacol. Toxicol. 2000. 40:67-95, 2000, Annual Reviews.

Wampler S., "Tackling Protocol Complexity," Good Clinical Practice Journal, 2000; vol. 7, No. 2: pp. 6-8.

* cited by examiner

FIG. 2 cancer_protocols_INSTANCE_00039 [instance of Cancer_Clinical_Protocol]

Label
CALGB 49802

Version
mgk 25Jan00

Title
Phase III Study of Adriamycin/Taxotere vs Adriamycin/Cytoxan for the Adjuvant treatment of Node Positive or High Risk Node Negative Breast Cancer

Authors
M.G. Public

Clinical Algorithm
CALGB 49802 Level 1

Reference
◆ MUSC PRN web page

Context Reference

Entry Criteria (1 values)

Protocol Name
CALGB 49802

Clinical State Name

Exclusion List
◆ Tumor of any size with direct extension to chest wall or skin (T4)
◆ Patient is pregnant or nursing

212

Inclusion List
◆ Histologically or cytologically confirmed invasive breast cancer
◆ 1-3 histologically involved axillary lymph nodes
◆ No evidence of metastatic disease (M0)
◆ Absolute neutrophil count of at least 1,500/mm3
◆ Platelet count of at least 100,000/mm3
◆ Left ventricular ejection fraction at rest at least 45% by MUGA
◆ Bilirubin no greater that 1.2 times upper limit of normal (ULN)
◆ Age 18-70
◆ Effective contraception required of fertile women
◆ No prior chemotherapy
◆ No prior radiotherapy
◆ No concurrent estrogen therapy

210 mgk_cancer_protocols_INSTANCE_00063 [instance of Consultation_Act.. _ ☐ ✕

| | |
|---|---|
| Label | mgk_cancer_protocols_INSTANCE_00063 [instance of Consul |

CALGB 49802: Collect Stratification Variabl

◆ Evaluate lymph node status
◆ Evaluate menopausal status
◆ Evaluate estrogen receptor status
◆ Evaluate progesterone receptor status Followed By  | V | C | + | − |

Rule In  | V | C | + | − |

Rule Out  | V | C | + | − |

References  | V | C | + | − |

© ProtocolElement

| Name | Documentation | Constraints |
|---|---|---|
| ProtocolElement | The superclass for all objects in the FastTrack protocol model. | |

Role

Abstract^A

Template Slots

| | Name | Type | Cardinality | Other Facets |
|---|---|---|---|---|
| 1010 | [S] disambiguationComments | Instance | multiple | classes={DisambiguationComment} |
| | [S] drillDown | Boolean | single | default={false} |
| 1012 | [S] encodingComments | String | single | |
| 1014 | [S] longDescription | String | single | |
| | [S] shortDescription | String | required single | |

FastTrack Protocol_INSTANCE_00212 [instance of Protocol]

ProtocolTitle
A Phase III Study of Paclitaxel via Weekly 1-Hour Infusion v

ProtocolIdentifier
CALGB 9840

OfficialSourceDocument
http://prn.musc.edu/research/protocol/deptmed/divhonc/br

ShortDescription
CALGB 9840

StudyChair
Andrew D. Seidman, M.D.

Sponsor
CALGB

QuickScreenCriterion — 1210
Breast Cancer

Sponsor
To compare "standard" (S) paclitaxel at 175 mg/m2 via 3-hour infusion every 3 weeks to "dose-dense" (DD) paclitaxel at 80 mg/m2 via 1-hour infusion every week

TrialStatus
Active

AccrualStatus
Open for accrual

TrialPhase
Phase III

TrialType
Cooperative group

Version
Update #1

VersionDate
December 15, 1998

EligibiltyCriteriaSet [V] [C] [+] [-]
◆ CALGB 9840 Eligibility Criteria — 1212

LongDescription

FirstVisit [V] [C] [+] [-]
Screening Visit

ProtocolSchemaDiagram [V] [C] [+] [-]
CALGB 9840 Schema — 1214

FIG. 12

2 day f/u for Visit 1 (DisambiguationProtocolEvent)

ShortDescription
2 day f/u for Visit 1

EventType
Treatment

LongDescription
These labs must be obtained in the morning.

Management Tasks
- Phone F/U
- Creatinine
- Ionized Ca
- Mg
- PO4
- CBC with Diff and plt

Incoming Links
- Visit 1 to Visit 1 f/u

EncodingComments

OutgoingLinks

DisambiguationComments
- Inconsistent tasks in tx plan and assessment

© TemporalLink (Connector_Metaclass)

| Name | Constraints | V C + − | Documentation |
|---|---|---|---|
| TemporalLink | | | This class a temporal constraint or anchoring between two visits. |
| Role | | | |
| Concrete | | | |

Template Slots                                                  v y c × + −

| | Name | Type | Cardinality | Other Facets |
|---|---|---|---|---|
| 1010 | [S] disambiguationComments | Instance | multiple | classes={DisambiguationComment} |
| | [S] dominant | Boolean | single | default={false} |
| | [S] drillDown | Boolean | single | default={false} |
| 510 | [S] encodingComments | String | single | |
| 1012 | [S] first_object°ᴵ | Instance | single | classes={ProtocolEvent} |
| 1518 | [S] longDescription | String | single | |
| 1516 | [S] maximumRelativeOffset | Integer | single | |
| 1522 | [S] minimumRelativeOffset | Integer | single | |
| 1520 | [S] offsetUnits | Symbol | required single | allowed-values={Years,Months,Week... |
| 1512 | [S] preferredRelativeOffset | Integer | single | |
| 1014 | [S] second_object°ᴵ | Instance | single | classes={ProtocolEvent} |
| | [S] shortDescription | String | required single | |

FastTrack Protocol_INSTANCE_00014 [Instance of Visit]

ShortDescription

Arm A Treatment Visit

PossibleVisitTransitions

- Arm A Treatment to Arm A Treatment Retry #1 — 1818
- Arm A Treatment to Long Term Followup
- Arm A Treatment Visit to Arm A Treatment Visit

1810

DataManagementTasks

- Submit Form C-116 — 1818
- Submit Form C-118
- Submit Form C-080
- Submit Form C-344 + Form C-080 (*)
- Submit Form C-344 + Form C-272 (*)
- Submit Form C-113 (*)
- Submit Form C-260 (*)
- Submit Form C-300 (*)

1814

PatientManagementTasks

- Confirm granulocytes >= 1500 / ul
- Confirm no G-CSF given in past 24 hours
- Give Dexmethosone 10 mg IV, 30 minutes
- Give Diphenydramine 50 mg IV, 30 minutes
- Give Cimetidine 300 mg IV, 30 minutes
- Give anti-emetics (*)
- Give Arm A Paclitaxel treatment — 1816
- Give G-CSF (*)
- Evaluate Patient Response
- Schedule next visit

1812

LongDescription

Arm A of the CALG 9840 consists of treatment with Paclitaxel 175 mg/m2 administered as a 3 hour infusion intravenously every three weeks. One cycle is equivalent to one infusion. Treatment cycles will be repeated every 21 days as long as the patient has stable or responding disease. Granulocyte count must be >= 1500/ul and platelet count must be >= 100,000 / ul on day 1 of each cycle. Patients should receive a minimum of two cycles of therapy, unless there is rapid disease progression (>50% increase in product of bi-dimensional measurements).

SiteLongDescription

SiteShortDescription

FIG. 18

ShortDescription

Give Arm A Paclitaxel treatment

LongDescription

Give Paclitaxel 175 mg/m2 IV, 3hours. This treatment is given to patients in Arm A of the CALGB 9840 protocol. It is given once every 3 weeks. One cycle is equivalent to one infusion. Granulocyte count must be >= 1500/ul and platelet count must be >= 100,000 / ul on day 1 of each cycle in order to proceed with the Paclitaxel infusion. Patients must receive the pre-medication prior to Paclitaxel infusion. If either the granulocyte or platelet count are not adequate, do not continue with treatment. Patients should receive a minimum of 2 cycles unless there is rapid disease progression.

Expected toxicities:

The dose-limiting toxicity of Paclitaxel is neutropenia. Other known toxicities include nausea and vomiting, diarrhea, stomatitis, mucositis, pharyngitis, typhlitis, ischemic colitis, bradycardia, atrial arrhythmia, hypotension, hypertension, sensory (taste), peripheral neuropathy, seizures, mood, hepatic encephalopathy, acute anaphylactoid and urticarial reactions, flushing, rash, pruritis, increased SGOT, SGPT, bilirubin and/or alkaline phosphatase, hepatic failure, hepatic necrosis, alopecia, fatigue, arthralgia, myalgia, light-headedness, myopathy, visual changes (sensation of flashing lights, blurred vision). Local infiltration with Paclitaxel will cause mild local symptoms (erythema, discomfort, induration) that usually resolve within a week. If infiltration occurs, there is the rare possibility of ulceration or rash. Seizure have been reported rarely in association with Paclitaxel use.

Dose Modifications:

Allergic reactions: Patients with grade 1 or 2 allergic reactions may have treatment continued without modifications. Patients with grade 3 or 4 allergic reactions who are responding to treatment may remain on protocol therapy after discussion with Study Chair. Such patients are at risk for recurrent allergic reactions. As a first maneuver, retreatment after premedication with oral recurrent allergic reactions. As a first maneuver, retreatment after premedication with oral dexamethasone 20 mg at 12 and 6 hours pre-administration of Paclitaxel, along with IV H1 and H2-receptor antagonist should be attempted. If necessary, thereafter, infusion rate adjustments will be considered and additional premedications will be administered. These patients must be informed of the potential risks of recurrent allergic reactions and must be carefully monitored.

Hematologic Toxicity: Patients are to be managed as clinically indicated. Colony stimulation factors (G-CSF) should be used in the manner

SiteLongDescription

FIG. 20

FastTrack Protocol_INSTANCE_00023 [instance of VisitToVisit Transition]

ShortDescription
Arm A Treatment to Arm A Treatment Retry #

First Object [V] [C] [+] [-]
Arm A Treatment Visit

Second Object [V] [C] [+] [-]
Arm A Treatment Retry #1

PrefrerredRelativeTime
7

MaximumRelativeTime
7

MinimumRelativeTime
7

LongDescription
If either granulocyte or platelet count are not adequate, blood counts should be repeated weekly and treatment should be instituted when there has been hematologic recovery. Patients receiving G-CSF are not eligible for re-treatment unless they have been off G-CSF for a minimum of 24 hours.

SiteLongDescription

☑ IsPreferredTransition — 2310

SiteShortDescription

DisambiguationComment

Name: DisambiguationComment

Documentation

Constraints

Role: Concrete

Template Slots

| Name | Type | Cardinality | Other Facets |
|---|---|---|---|
| 2610 [S] conceptualProtocolSection | Symbol | multiple | allowed-values={Protocol Summary,... |
| 2612 [S] documentReferences | Instance | multiple | classes={DocumentReference} |
| 2614 [S] Impact Type | Symbol | multiple | allowed-values={Safety,Efficacy-prim.. |
| 2616 [S] Issue | String | single | |
| 2618 [S] Potential Impact | String | single | |
| 2620 [S] Protocol text | String | single | |
| 2622 [S] Recommendation | String | single | |
| 2624 [S] Severity Level | Symbol | single | allowed-values={Level One,LevenTw.. |
| [S] Short Description | String | single | |

FIG. 26

31 (Document Reference)

PageNumber
31

SectionReferenceNumber
11.1.2

LiteralSponsorSectionName
VisualFunction and MSFC Practice Tests

AddlDocRefInfo
Examining Technician instructions

ProtocolText
"...performed three times within 35 days prior to randomization, with at least 5 days between any two evaluations.."

EncodingComments

FIG. 37

DISAMBIGUATION FINDINGS

| Item | Impact Type | Protocol Section | Description | Document Reference |
|---|---|---|---|---|
| 1 | Safety Efficacy-primary Efficacy-secondary | Protocol Summary Study Flow Chart | Issue:<br>The description in the Protocol Synopsis of when assessments should be performed after 16 weeks is not consistent with Appendix I Schedule of Assessments.<br><br>Potential Impact:<br>Confusion as to when to perform these evaluations (clinical parameters and safety assessments) could result in inconsistent and inaccurate collection of data for the study.<br><br>Recommendation:<br>Revise sentence in the Protocol Synopsis to read, "After 16 weeks these evaluations will be performed every two to "four" months…" in order to be consistent with the timepoints indicated in Appendix I Schedule of Assessments. | *Pg. 12; Section Protocol Synopsis; Procedure; Paragraph 6:*<br>"Clinical parameters (ACR core set) and safety assessments (adverse events and laboratory parameters) will be performed at baseline and then at monthly intervals up to 16 weeks. After 16 weeks these evaluations will be performed every two to three months, up to 104 weeks." |

FIG. 40

| Item | Impact Type | Protocol Section | Description | Document Reference |
|---|---|---|---|---|
| 4 | Safety Accrual | Screening Assessments Study Flow Chart | Issue:<br>The protocol text specifies that if an analysis with evidence of seropositivity was performed within 6 months before screening, then rheumatoid factor testing will not have to be performed at screening. However, this is not noted in Appendix I Schedule of Assessments.<br><br>Potential Impact:<br>Unnecessary analysis performed at screening.<br><br>Recommendation:<br>Add a footnote to the Rheumatoid Factor assessment in Appendix I to clarify that documented evidence of seropositivity is acceptable as screening data if obtained within 6 months before screening. | *Pg. 28; Section 8.6.2; Rheumatoid Factor:* "Unless there is documented evidence of rheumatoid factor titre within 6 months before screening a blood sample for this analysis will be taken."<br><br>*Pg. 41; Section Appendix I; Schedule of Assessments* |

FIG. 41

PROTOCOL DISAMBIGUATION USING A MODEL-BASED METHODOLOGY

CROSS-REFERENCES

This is a Continuation-In-Part of parent U.S. patent application Ser. No. 09/584,936, filed 31 May 2000. The parent application is commonly owned with the subject application and is incorporated herein by reference in its entirety.

BACKGROUND

1. Field of the Invention

The invention relates to the evaluation of clinical trial protocols, and more particularly to a methodology and structures for assisting reviewers in the identification of operational uncertainties in clinical trial protocols.

2. References

The following documents are incorporated by reference herein:

DataEdge LLC. Indexes of clinical study complexity, 1993-1999. In: Mathieu M P, editor. Parexel's Pharmaceutical R&D Statistical Sourcebook 2000. Waltham, Mass.: Parexel International Corp; 2000. p. 66.

DataEdge LLC. Indexes of clinical trial costs per patient, 1993-1999. In: Mathieu M P, editor. Parexel's Pharmaceutical R&D Statistical Sourcebook 2000. Waltham, Mass.: Parexel International Corp; 2000. p. 67.

Grosso W E, et. al., "Knowledge Modeling at the Millennium (The Design and Evolution of Protégé-2000)," SMI Report Number: SMI-1999-0801 (1999), available at http://smi-web.stanford.edu/pubs/SMI_Abstracts/SMI-1999-0801.html, visited Jan. 1, 2000.

Holford N H, Kimko H C, Monteleone J P, Peck C C. Simulation of clinical trials. Annu Rev Pharmacol Toxicol 2000; 40:209-34.

Howard R A, Matheson J E, editors. Readings on the principles and applications of decision analysis. Menlo Park, Calif.: Strategic Decision Group; 1983.

Hulley S B, Cummings S R, Browner W S, Grady D, Hearst N, Newman T B. Designing clinical research: An epidemiologic approach. Second ed. Philadelphia: Lippincott Williams & Wilkins; 2001.

International Conference on Harmonisation. E6: Guideline for good clinical practice. URL: www.ifphma.org/ich5e.html. Accessed: 31 Aug. 2001.

International Conference on Harmonisation. E8: General considerations for clinical trials. URL: www.ifpma.org/ich5e.html. Accessed: 31 Aug. 2001.

Kroll J A, de Bruin A, Getz K, Eschmann K, Zisson S. Study conduct delays are getting worse. In: Kroll JA, editor. An Industry In Evolution. Second ed. Boston, Mass.: CenterWatch; 1999. p. 99.

Matheson D, Matheson J E. The smart organization: Creating value through strategic R&D. Boston, Mass.: Harvard Business School Press; 1998.

McNamee P, Celona J. Decision analysis for the professional with Supertree: Scientific Press; 1987.

Musen M A, Gennari J H, Eriksson H, Tu S W, Puerta A R. Protege-II: Computer support for development of intelligent systems from libraries of components. Medinfo 1995; 8(1):766-70.

Musen M A, Rohn J A, Fagan L M, & Shortliffe E H, "Knowledge engineering for a clinical trial advice system: Uncovering errors in protocol specification," Report KSL-85-51, Proceedings AAMSI Congress 1986 (Levy, A. H. and Williams, B. T., eds.), pp. 24-27, Anaheim Calif., May 1986.

Musen M A. Domain ontologies in software engineering: Use of Protege with the EON architecture. Methods Inf Med 1998; 37(4-5):540-50.

Piantadosi S. Clinical trials: A methodologic perspective. New York, N.Y.: John Wiley & Sons; 1997.

Sheiner L B, Steimer J L. Pharmacokinetic/pharmacodynamic modeling in drug development. Annu Rev Pharmacol Toxicol 2000; 40:67-95.

Spilker B. Guide to Clinical Studies and Developing Protocols. New York, N.Y.: Raven Press; 1984.

Spilker B. Guide to Clinical Trials. New York, N.Y.: Raven Press; 1991.

Wampler S. Tackling Protocol Complexity. Good Clinical Practice J 2000; 7(2):6-8.

3. Description of Related Art

Clinical trial protocols are designed to produce scientifically sound new knowledge about the safety, efficacy or specific therapeutic characteristics of a new drug or treatment combination. Clinical trial protocols developed using modern study design principles have well-understood statistical hypothesis testing and internal validity characteristics. Thus, modern clinical studies are designed to deliver the most supportable scientific knowledge with the smallest number of study subjects. Despite these more efficient study designs, the complexity and associated costs of executing new protocols continue to increase.

The rising complexity of current protocol designs has resulted in a dramatic increase in the operational management overhead required to initiate, execute, and complete a clinical trial successfully within budget and time frame. With the increasing number of patients, investigators, locations, and countries involved in a given trial, it is not surprising that a many clinical trials have significant operational issues that cause substantial cost/time over-runs or outright trial failures.

A distinction between scientific versus operational issues in clinical trials planning and execution is important. A scientific issue arises due to the limited state of current knowledge about the trial agent(s) pharmacologic and therapeutic properties in the experimental clinical situation. This lack of scientific knowledge is precisely the reason a well-designed clinical trial is required. Scientific issues are ethically justified and do not indicate any problem with the clinical trial protocol. Operational issues arise because of unforeseen difficulties in executing the trial within the strict parameters or assumptions embedded implicitly or explicitly within the protocol design. In this case, the protocol designers may not have been able to predict the difficulties the field organization or clinical investigators may have in operationalizing specific study design components.

Operational deficiencies can be costly to an organization, especially if they require an amendment to the protocol during execution of the trial. Even simple amendments have substantial costs, including the internal overhead of detecting the need for an amendment, costs for creating the amendment, internal approvals costs for releasing the amendment, costs for disseminating the amendment and the follow-up effort to ensure that the amendment has been incorporated into the clinical trials process at a potentially large number of the trial sites. The cost of an amendment also includes the opportunity costs due to study completion delays or data analysis impact due to inconsistent operational behavior at the trial sites.

Amendments are only the most visible and more costly manifestation of a spectrum of ways in which operational deficiencies can impact an organization. A large number of operational issues are handled via formal and informal communications between study project managers and clinical trials sites. Thus the volume of faxes and telephone calls can be another "cost" which directly affects team productivity and trial site performance but is not as visible as a trial amendment.

At most large clinical development organizations, concern about protocol design quality has spawned the creation of Protocol Review Committees (PRCs). Although specifics vary widely, the role of the PRC is to provide a centralized resource for the critical examination of a proposed protocol in a "near-final" form. Unlike Institutional Review Boards who are concerned about patient safety, risk/benefit and informed consent, the focus of the PRC is on scientific merit, study validity, and the appropriate use of scarce clinical development resources. Many PRCs include representatives from clinical operations and a few include clinical trial sites so that the operational issues that may be embedded within or implied by a proposed trial design can be examined.

Many organizations that have implemented PRCs now require every protocol to be reviewed and approved by the committee prior to its release to the clinical operations team for field deployment. In addition, many PRC members state that a review by the committee often results in substantial changes to the original protocol. Protocol Review Committees bring together substantial skills and corporate institutional experience, representing an enormous investment of highly trained personnel. For the organizations that have committed to this approach, this investment is deemed to be justifiable, given the high stakes and resources committed to the execution and success of each trial.

PRC reviews do seem to have a positive contribution to the operational quality of reviewed protocols. But the cost of such reviews is large. PRCs generally require highly trained, expensive senior people to perform time-consuming, detailed review of every protocol prior to internal approval. The man-hours consumed in analyzing a proposed protocol, discussing the findings at a PRC meeting, presenting the findings to the protocol author and then repeating the process in a limited manner after the protocol is revised represent a huge hidden cost. As PRC members leave or rotate, the quality and quantity of protocols reviewed by the PRC may vary widely. Thus, while PRC reviews may be effective, they are neither scalable nor repeatable.

In addition to or instead of forming Protocol Review Committees, many organizations have instituted other methods for improving the quality of the protocol during its initial creation. Templates, checklists, and previously approved protocols are common materials provided to protocol authors to assist with the improvement of the quality of their initial protocol designs. These methods have numerous drawbacks, however, that significantly limit their usefulness. First, most paper-based methods are static. That is, these methods are not easily updated, disseminated, and then incorporated into the protocol writer's daily routine. Thus, it is often the case that protocols developed with these tools continue to make the same operational mistakes long after the organization has updated the reference materials.

Second, as people leave the organization, the institutional knowledge of what makes a protocol "work" within that organization is lost. If the employee was a member of the Protocol Review Committee, this loss of institutional knowledge is even more extensive, impacting the entire range of protocols reviewed by the PRC.

Third, organizational mergers and alliances result in widely disparate approaches, assumptions, and standard operating procedures for designing protocols. Operational knowledge unique to one organization or to a specific therapeutic area tends to remain within the original organization or therapeutic area and therefore not benefit the combined organization. Hard-earned (and expensive) experience-based knowledge diffusion occurs only if and when people from one organization migrate into similar positions within the second organization. Of course, this migration results in the loss of operational knowledge from the original clinical operations group.

Accordingly, there is an urgent need for a methodology and tools that will assist the reviewers of clinical trial protocols in identifying operational uncertainties early, before a clinical trial begins according to the protocol.

SUMMARY OF THE INVENTION

The invention involves a new methodology for significantly reducing the risk of protocol inconsistencies and ambiguities that could lead to operational failures. The methodology typically is applied prospectively before a trial is begun, when changes in protocol design are the least disruptive and engender minimal cost. The methodology also provides a means for capturing, formalizing, and reusing an institution's implicit operational knowledge so that future proposed protocol designs can be evaluated for potential operational problems as well.

According to the invention, roughly described, an analyst encodes features of a protocol into a highly structured, formal model of a clinical protocol that has been created specifically to capture issues that tend to cause operational difficulties. The process forces the analyst to look for specific parameters in the text version of the protocol, the absence of which, or any ambiguities or vagueness in which, represent operational uncertainties that can adversely impact the progress of the study.

The system creates a database of the protocol as encoded, and can display the protocol schema in the form of a graphical network of protocol events and temporal links. In one aspect, the analyst encodes descriptions of each operational uncertainty uncovered, directly into the database in a manner that is associated with a particular relevant one of the objects in the network. The system then can display the network in graphical-visual form, with the associated graphical object set forth with a human-perceptible indication that it has an operational uncertainty associated therewith. For example, it can be displayed in a different color. In a further aspect, the viewer can "drill down" on an object indicating the presence of an operational uncertainty, and the system will open up a window displaying the encoded description of the uncertainty.

The database can for example be an object-oriented database, in which case the descriptions of operational uncertainties can be encapsulated into separate protocol disambiguation comment objects. The object class definitions for various protocol objects then can include slots for pointing to any protocol disambiguation comment object(s) associated therewith.

In addition, it has been discovered that the temporal relationships among protocol events are a particularly fertile area for operational uncertainties. More frequently than many other parameters, these time constraints are either omitted completely from the text protocol, or are specified but only vaguely, or are specified inconsistently in different parts of the protocol. Accordingly, in an aspect of the invention, the formal model of the clinical trial protocol includes template slots for encoding any temporal constraints between or among protocol events. In simple embodiments the model allows entry of only a single time value for each temporal constraint. In more sophisticated embodiments the model allows entry of a permissible range of time periods, or minimum, maximum and base time periods, or a probability function.

In an embodiment, the database is an object-oriented database and the model includes protocol event objects describing protocol events, and temporal link objects describing temporal constraints between protocol event objects. The temporal constraint slots are part of the class definition for temporal link objects. If the analyst uncovers an operational uncertainty concerning the time periods allowed between one protocol event and another, that uncertainty then can be described in a disambiguation comment object which is then associated with the relevant temporal link object. When displayed in graphical-visual form, temporal link objects are shown as arrows pointing from an originating protocol event object to a target protocol event object, and the color of the arrow is made to depend on whether the database includes a protocol disambiguation comment object associated with the temporal link object.

BRIEF DESCRIPTION OF THE DRAWINGS

The invention will be described with respect to specific embodiments thereof, and reference will be made to the drawings, in which:

FIGS. 2-8 are screen shots of an example for an Intelligent Clinical Protocol (iCP) database.

FIGS. 10, 13, 15, 26 and 36 illustrate class definitions for several classes in the class structure of FIG. 9.

FIGS. 11, 12 and 17-25 are screen shots of screens produced by Protégé 2000, and help illustrate the relationship between a protocol meta-model and an example individual clinical trial protocol.

FIG. 14 illustrates an example object instantiated according to the DisambiguationProtocolEvent class in the class structure of FIG. 9.

FIG. 16 illustrates an example object instantiated according to the TemporalLink class in the class structure of FIG. 9.

FIG. 37 illustrates a an example object instantiated according to the DocumentReference class in the class structure of FIG. 9.

FIGS. 40 and 41 illustrate two example rows from a Protocol Disambiguation report table output by the reporter tool.

DETAILED DESCRIPTION

Figure 1:
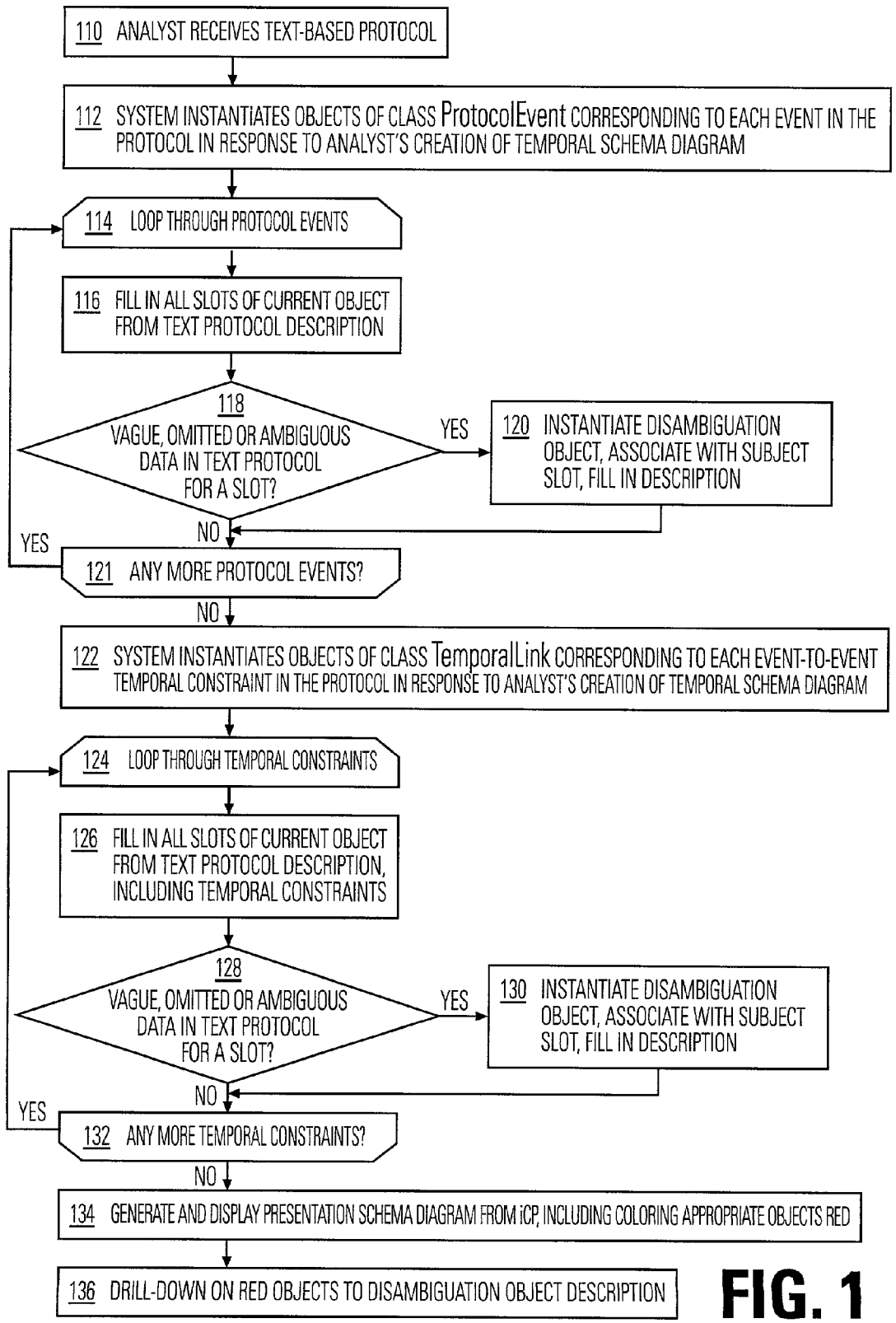
FIG. 1 is a flowchart illustrating tasks that an analyzer of a text-based clinical trial protocol can perform in order to help identify operational uncertainties in a protocol.

In the parent patent application, there is described a system which defines, manages and evaluates clinical trial protocols in an overall end-to-end manner. The system starts with the creation of protocol meta-models by a central authority, and ends with the conduct of trials by clinical sites, who then report back electronically for near-real-time monitoring by study sponsors and for analysis by the central authority. The central authority first creates protocol meta-models, one for each of several different disease categories, and makes them available to protocol encoders. The protocol encoder chooses the meta-model appropriate for the relevant disease category, and encodes the clinical trial protocol within the selected meta-model. The resulting protocol database is referred to herein as an Intelligent Clinical Protocol (iCP), and the iCP drives all downstream problem solvers including a problem solver that indicates to the clinician at a study site exactly what tasks are to be performed at each patient visit. These tasks can include both patient management tasks, such as administering a drug or taking a measurement, and also data management tasks, such as completing and submitting a particular case report form (CRF). The workflow graph embedded in the protocol database advantageously also instructs the proper time for the clinician to obtain informed consent from a patient during the eligibility screening process, and when to perform future tasks, such as the acceptable date range for the next patient visit. In the embodiments described herein, the protocol metamodels constitute the highly structured, formal models that are used to encode a clinical trial protocol and to identify any operational uncertainties contained within the text version of the protocol.

The protocol meta-models are created using a meta-model authoring tool. Protégé 2000 is an example of a tool that can be used as a meta-model authoring tool. Protégé 2000 is described in a number of publications including William E. Grosso, et. al., "Knowledge Modeling at the Millennium (The Design and Evolution of Protégé-2000)," SMI Report Number: SMI-1999-0801 (1999), available at http://smi-web.stanford.edu/pubs/SMI_Abstracts/SMI-1999-0801.html, visited Jan. 1, 2000, incorporated by reference herein. In brief summary, Protégé 2000 is a tool that helps users build other tools that are custom-tailored to assist with knowledge-acquisition for expert systems in specific application areas. It allows a user to define "generic ontologies" for different categories of endeavor, and then to define "domain-specific ontologies" for the application of the generic ontology to more specific situations. In many ways, Protégé 2000 assumes that the different generic ontologies differ from each other by major categories of medical endeavors (such as medical diagnosis versus clinical trials), and the domain-specific ontologies differ from each other by disease category. In the present embodiment, however, all ontologies are within the category of medical endeavor known as clinical trials and protocols. The different generic ontologies correspond to different meta-models, which differ from each other by disease category. In this sense, the generic ontologies produced by Protégé in the present embodiment are directed to a much more specific domain than those produced in other applications of Protégé 2000.

Since the meta-models include numerous building blocks as well as many options for patient eligibility criteria, a wide variety of different kinds of clinical trial protocols, both simple and complex, can be designed. These meta-models are provided to clinical trial protocol encoders who use them, preferably again with the assistance of Protégé 2000, to encode individual clinical trial protocols.

In order to encode a clinical trial protocol, a user first selects the appropriate meta-model and then uses the authoring tool to design and store the protocol. Again, one embodiment of the authoring tool for encoding the protocol is based on Protégé 2000. The output is the iCP database, containing all the significant required elements of a protocol.

Conceptually, an iCP database is a computerized data structure that encodes most significant operational aspects of a clinical protocol, including eligibility criteria, randomization options, treatment sequences, data requirements, and protocol modifications based on patient outcomes or complications. In the embodiments described herein, the iCP is an object-oriented database, but databases deriving from other database paradigms (such as a relational database) can be used instead. The iCP structure can be readily extended to encompass new concepts, new drugs, and new testing procedures as required by new drugs and protocols. The iCP database is used by most software modules in the overall system to ensure that all protocol parameters, treatment decisions, and testing procedures are followed.

The iCP database can be thought of as being similar to the CAD/CAM tools used in manufacturing. For example, a CAD/CAM model of an airplane contains objects which represent various components of an airplane, such as engines, wings, and fuselage. Each component has a number of additional attributes specific to that component—engines have thrust and fuel consumption; wings have lift and weight. By constructing a comprehensive model of an airplane, numerous different types of simulations can be executed using the same model to ensure consistent results, such as flight characteristics, passenger/revenue projections, maintenance schedules. And finally, the completed CAD/CAM simulations automatically produced drawings and manufacturing specifications to accelerate actual production. While an iCP database differs from the CAD/CAM model in important ways, it too provides a comprehensive model of a clinical protocol so as to support consistent tools created for problems such as accrual, patient screening and workflow management. By using a comprehensive model and a unifying standard vocabulary, all tools behave according to the protocol specifications.

As used herein, the term "database" does not necessarily imply any unity of structure. For example, two or more separate databases, when considered together, still constitute a "database" as that term is used herein.

The iCP data structures can be used by multiple tools to ensure that the tool performs in strict compliance with the clinical protocol requirements. For example, a patient recruitment simulation tool can use the eligibility criteria encoded into an iCP data structure, and a workflow management tool uses the visit-specific task guidelines and data capture requirements encoded into the iCP data structure. The behavior of all such tools will be consistent with the protocol because they all use the same iCP database.

The iCP database is used to drive all downstream "problem solvers" such as electronic CRF generators, and assures that those applications are revised automatically as the protocol changes. This assures protocol compliance. The iCP authoring tool draws on external knowledge bases to help trial designers, and makes available a library of re-usable protocol "modules" that can be incorporated in new trials, saving time and cost and enabling a clinical trial protocol design process that is more akin to customization than to the current "every trial unique" model.

FIGS. 11-25 are screen shots of screens produced by Protégé 2000, and will help illustrate the relationship between a protocol meta-model and an example individual clinical trial protocol. FIG. 11 is a screen shot illustrating the overall class structure in the left-hand pane 1110. Of particular interest to the present discussion is the class 1112, called "FastTrack-Class," also often referred to herein as the ProtocolElement class), and the classes under class 1112. ProtocolElement 1112 and those below it represent an example of a protocol meta-model. This particular meta-model is not specific to a single disease category.

The right-hand pane 1114 of the screen shot of FIG. 11 sets forth the various slots that have been established for a selected one of the classes in the left-hand pane 1110. In the image of FIG. 11, the "protocol" class 1116, a subclass of ProtocolElement 1112, has been selected (as indicated by the border). In the right-hand pane 1114, specifically in the window 1118, the individual slots for protocol class 1116 are shown. Only some of the slots are pertinent to the present discussion; those not discussed herein are not important for an understanding of the invention. It can be seen that several of the slots in the window 1118 contain "facets" which, for some slots, define a limited set of "values" that can be stored in the particular slot. For example, the slot "quickScreenCriterion" 1120 can take on only the specific values "prostate cancer," "colorectal cancer," "breast cancer," etc.

FIG. 12 is a screen shot of a particular instance of class "protocol" in FIG. 11, specifically a protocol object having identifier CALGB 9840. It can be seen that each of the slots defined for protocol class 1116 has been filled in with specific values in the protocol class object instance of FIG. 12. Whereas FIG. 11 illustrates an aspect of a clinical trial protocol meta-model, FIG. 12 illustrates the top-level object of an actual iCP designated CALGB 9840. For example, it can be seen that for the iCP CALGB 9840, the slot "quickScreen-Criterion" 1120 (FIG. 11) has been filled in by the protocol encoder as "Breast Cancer" (item 1210 in FIG. 12), which is one of the available values 1122 for the quickScreenCriterion slot 1120 in FIG. 11. In addition, the protocol encoder has also filled in "CALGB 9840 Eligibility Criteria", an instance of EligibilityCriteriaSet class 1124, for an EligibilityCriteriaSet slot (not shown in FIG. 11) of the protocol class object. Essentially, therefore, the protocol class object of FIG. 12 includes a pointer to another object identifying the "further eligibility criteria" for iCP CALGB 9840.

As used herein, the "identification" of an item of information does not necessarily require the direct specification of that item of information. Information can be "identified" in a field by simply referring to the actual information through one or more layers of indirection, or by identifying one or more items of different information which are together sufficient to determine the actual item of information. Similarly, when a data object is said to "describe" an aspect of the protocol, there is no requirement that the entire description be self-contained within the data object. For example, part of the description can be physically located elsewhere, and merely be either explicitly or implicitly associated with the data object.

Figure 17:
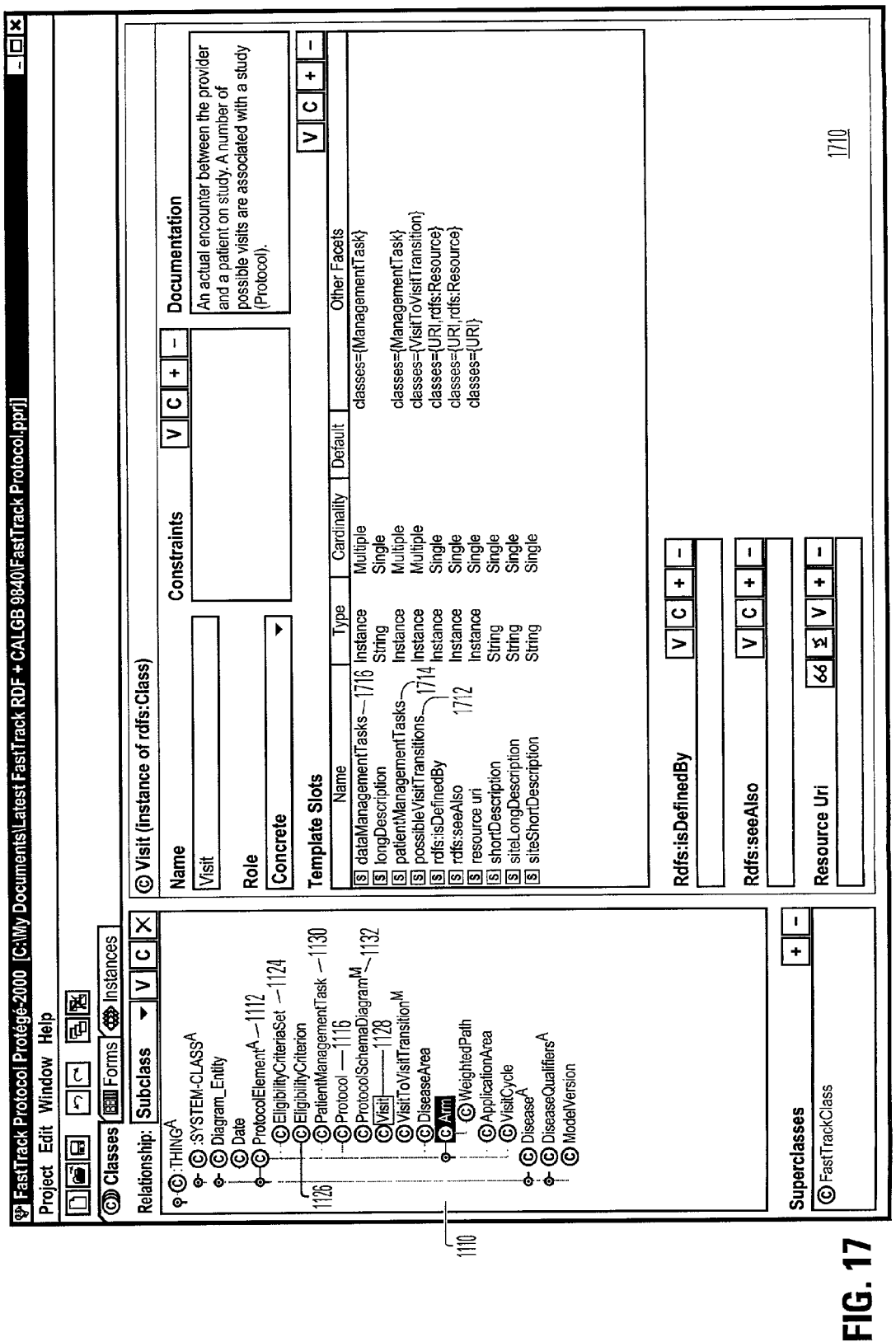
Figure 19:
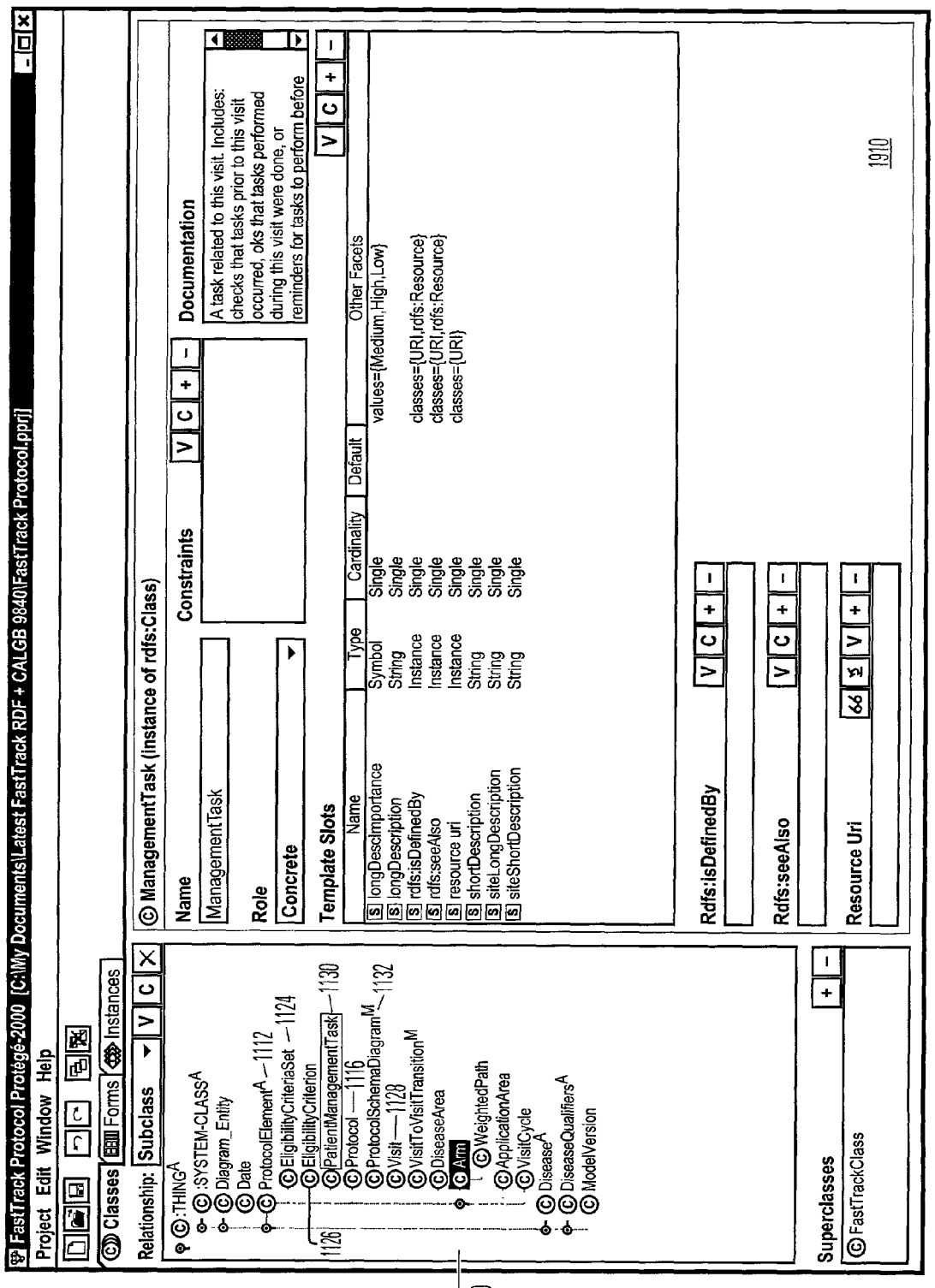

An iCP contains the protocol workflow in the form of patient visits, management tasks to take place during a visit, and transitions from one visit to another. The right-hand pane 1710 of FIG. 17 illustrates the slots available for an object instance of the class "visit" 1128. It can be seen that in addition to a slot 1712 for possible visit transitions, the Visit class also includes a slot 1714 for patient management tasks as well as another slot 1716 for data management tasks. In other words, a clinical trial protocol prepared using this clinical trial protocol meta-model can include instructions to clinical personnel not only for patient management tasks (such as administer certain medication or take certain tests), but also data management tasks (such as to complete certain CRFs). The terms "visit" and "protocol event" are used interchangeably herein. Both are intended to refer to events called for in a protocol, and neither requires any actual patient contact, whether remote or in person.

FIG. 18 illustrates a particular instance of visit class 1128, which is included in the CALGB 9840 iCP. As can be seen, it includes a window 1810 containing the possible visit transitions, a window 1812 containing the patient management tasks, and a window 1816 showing the data management tasks for a particular visit referred to as "Arm A treatment visit". The data management tasks and patient management tasks are all instance of the "PatientManagementTask" class 1130 (FIG. 11), the slots of which are set forth in the right-hand pane 1910 of FIG. 19. As with the EligibilityCriterion class 1126 (FIG. 14), the slots available to a protocol encoder in a PatientManagementTask object are mostly text fields.

Figure 21:
Figure 22:
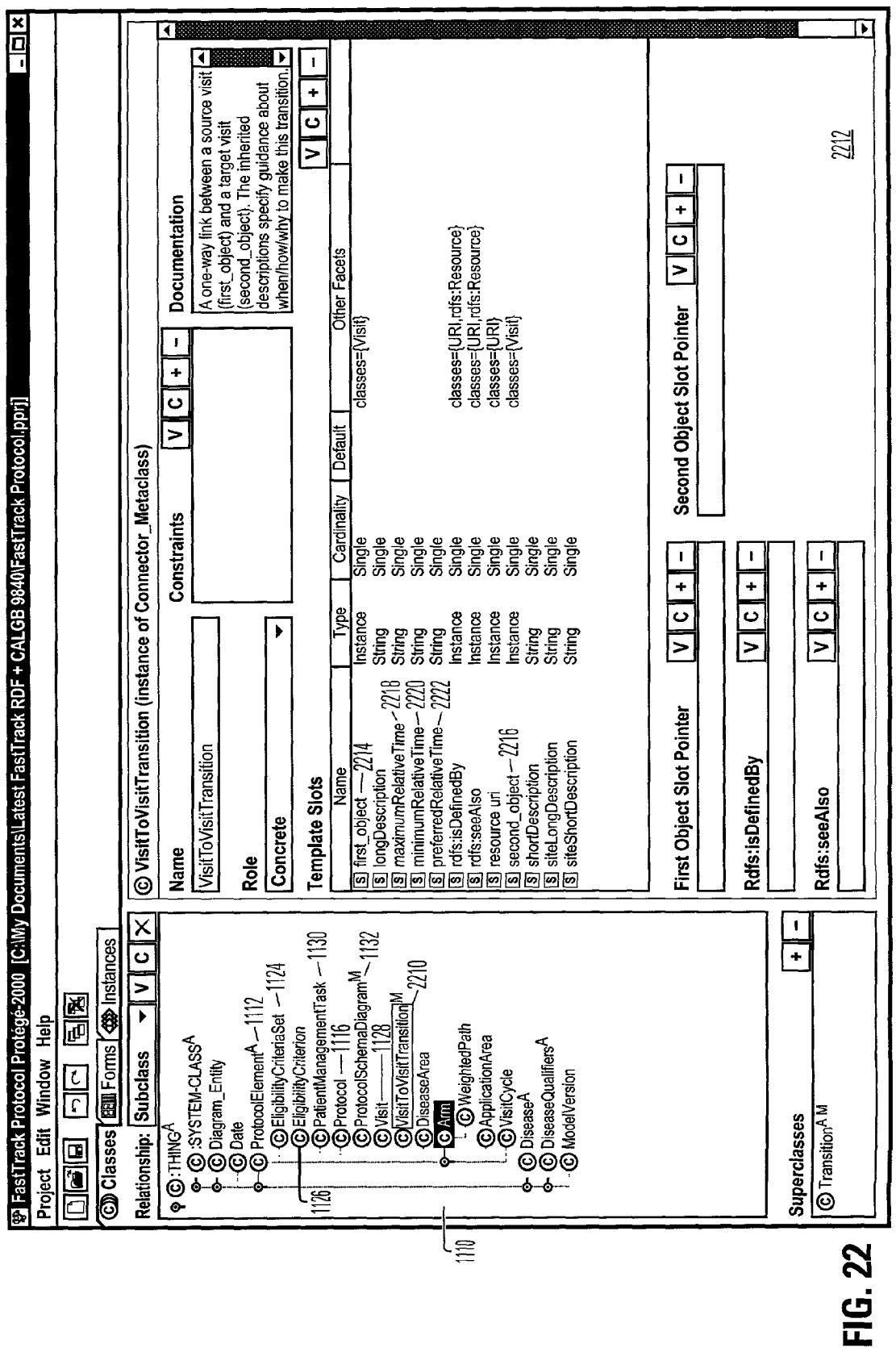

FIG. 20 illustrates the PatientManagementTask object 1816 (FIG. 18), "Give Arm A Paclitaxel Treatment." Similarly, FIG. 21 illustrates the PatientManagementTask object 1818, "Submit Form C-116". The kinds of data management tasks which can be included in an iCP according to the clinical trial protocol meta-model include, for example, tasks calling for clinical personnel to submit a particular form, and a task calling for clinical personnel to obtain informed consent.

Returning to FIG. 17, the values that a protocol encoder places in the slot 1712 of a visit class 1128 object are themselves instances of VisitToVisitTransition class 2210 (FIG. 22) in the meta-model. The right-hand pane 2212 shows the slots which are available in an object of the VisitToVisitTransition class 2210. As can be seen, it includes a slot 2214 which points to the first visit object of the transition, another slot 2216 which points to a second visit object of the transition, and three slots 2218, 2220 and 2222 in which the protocol encoder provides the minimum, maximum and preferred relative time of the transition. FIG. 23 shows the contents of a VisitToVisitTransition object 1818 (FIG. 18) in the CALGB 9840 iCP.

Figure 24:
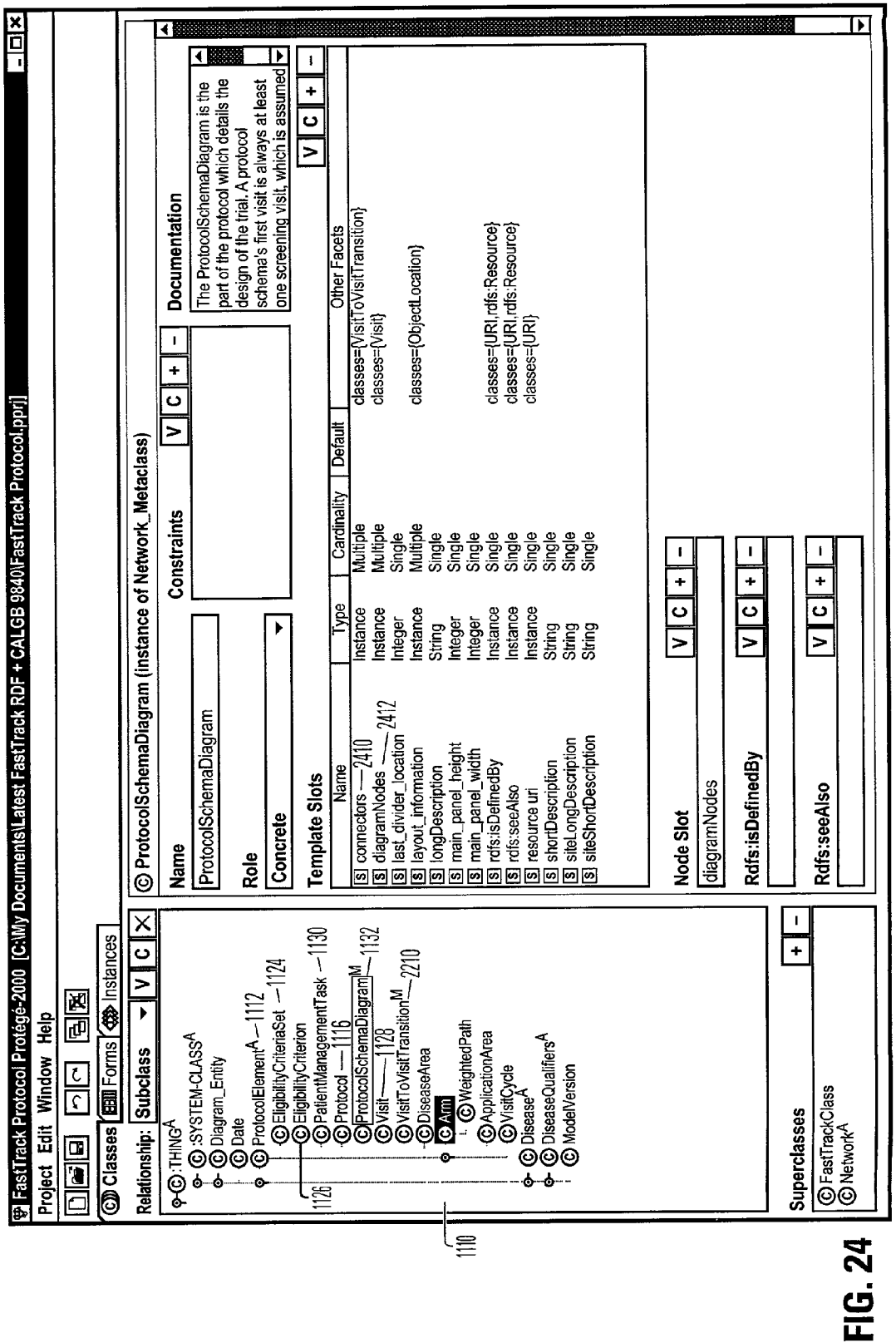
Figure 25:
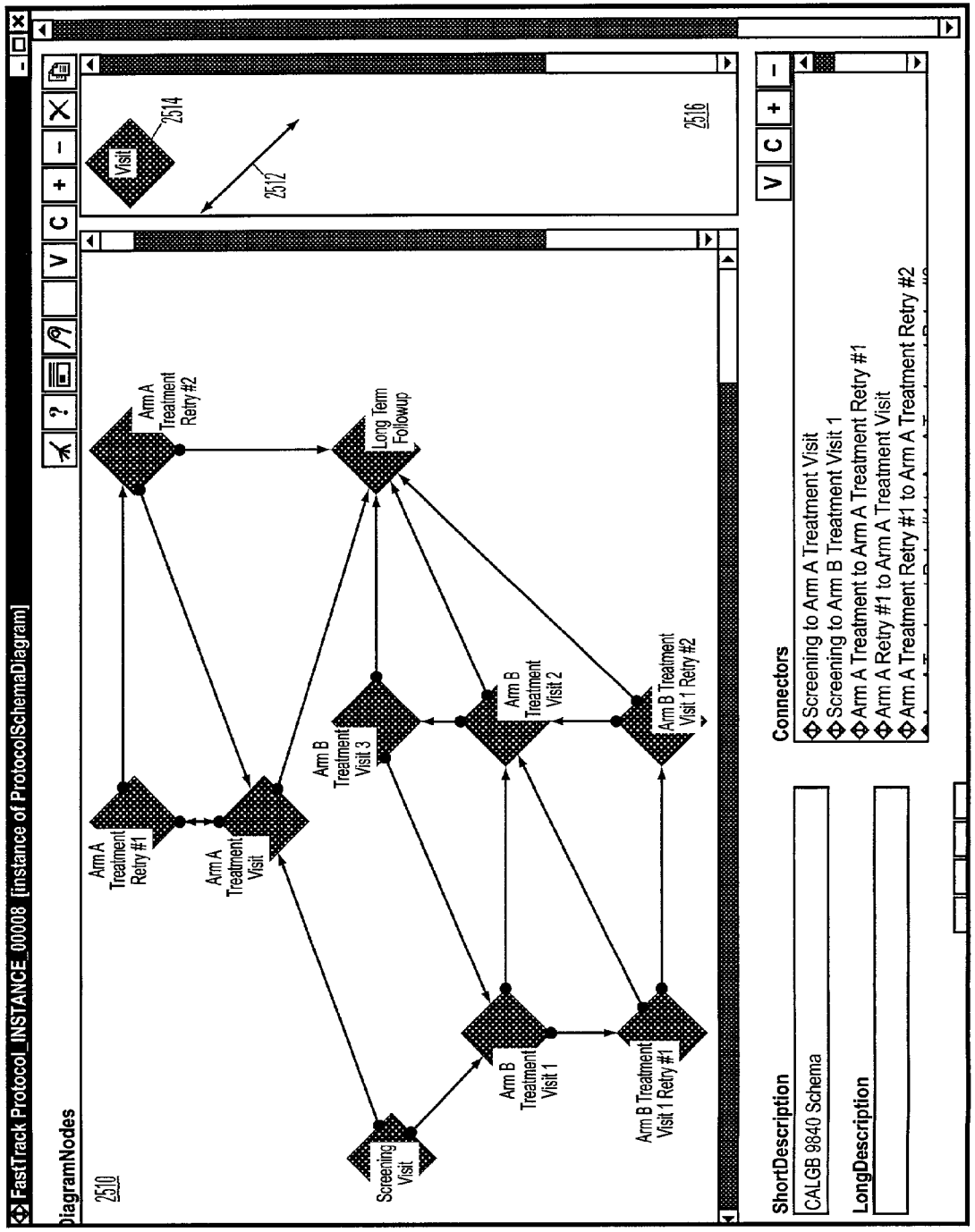

In addition to being kept in the form of Visit objects, management task objects and VisitToVisitTransition objects, the protocol meta-model also allows an iCP to keep the protocol schema in a graphical or diagrammatic form as well. In fact, it is the graphical form that protocol encoders typically use, with intuitive drag-and-drop and drill-down behaviors, to encode clinical trial protocols using Protégé 2000. In the protocol meta-model, a slot 1134 is provided in the Protocol object class 1116 for pointing to an object of the ProtocolSchemaDiagram class 1132 (FIG. 11). FIG. 24 shows the slots available for ProtocolSchemaDiagram class 1132. As can be seen, they include a slot 2410 for diagrammatic connectors, and another slot 2412 for diagram nodes. The diagram connectors are merely the VisitToVisitTransition objects described previously, and the diagram nodes are merely the Visit objects described previously. FIG. 25 illustrates the ProtocolSchemaDiagram object 1214 (FIG. 12) in the CALGB 9840 iCP. It can be seen that the entire clinical trial protocol schema is illustrated graphically in pane 2510, and the available components of the graph (connector objects 2512 and visit objects 2514) are available in pane 1516 for dragging to desired locations on the graph.

FIGS. 2-8 are screen shots of another example iCP database, created and displayed by Protégé 2000 as an authoring tool. This iCP encodes clinical trial protocol labeled CALGB 49802, and differs from the CALGB 9840 iCP in that CALGB 49802 was encoded using a starting meta-model that was already specific to a specific disease area, namely cancer. It will be appreciated that in other embodiments, the meta-models can be even more disease specific, for example meta-models directed specifically to breast cancer, prostate cancer and so on.

FIG. 2 is a screen shot of the top level of the CALGB 49802 iCP database. The screen shot sets forth all of the text fields of the protocol, as well as a list 210 of patient inclusion criteria and a list 212 of patient exclusion criteria.

Figure 3:
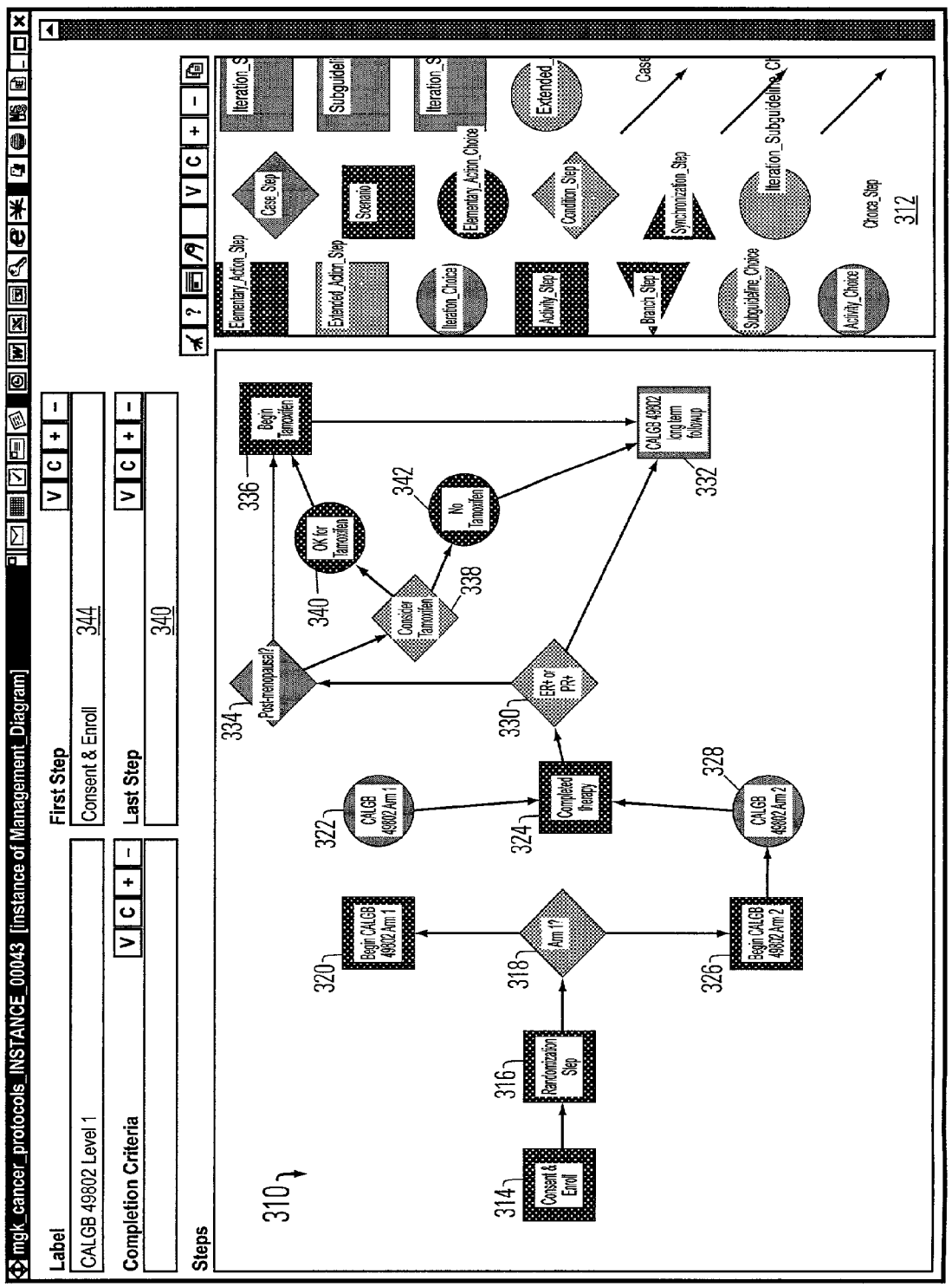

FIG. 3 is a screen shot of the Management_Diagram class object for the iCP, illustrating the workflow diagram for the clinical trial protocol of FIG. 2. The workflow diagram sets forth the clinical algorithm, that is, the sequence of steps, decisions and actions that the protocol specification requires to take place during the course of treating a patient under the particular protocol. The algorithm is maintained as sets of tasks organized as a graph 310, illustrated in the left-hand pane of the screen shot of FIG. 3. The protocol encoder adds steps and/or decision objects to the graph by selecting the desired type of object from the palate 312 in the right-hand pane of the screen shot of FIG. 3, and instantiating them at the desired position in the graph 310. Buried beneath each object in the graph 310 are fields which the protocol encoder completes in order to provide the required details about each step, decision or action. The user interface of the authoring tool allows the encoder to drill down below each object in the graph 310 by double-clicking on the desired object. The Management_Diagram object for the iCP also specifies a First Step (field 344), pointing to Consent & Enroll step 314, and a Last Step (field 346), which is blank.

Referring to the graph 310, it can be seen that the workflow diagram begins with a "Consent & Enroll" object 314. This step, which is described in more detail below, includes sub-steps of obtaining patient informed consent, evaluating the patient's medical information against the eligibility criteria for the subject clinical trial protocol, and if all such criteria are satisfied, enrolling the patient in the trial.

After consent and enrollment, step 316 is a randomization step. If the patient is assigned to Arm 1 of the protocol (step 318), then workflow continues with the "Begin CALGB 49802 Arm 1" step object 320. In this Arm, in step 322, procedures are performed according Arm 1 of the study, and workflow continues with the "Completed Therapy" step 324. If in step 318 the patient was assigned Arm 2, then workflow continues at the "Begin CALGB 49802 Arm 2" step 326. Workflow then continues with step 328, in which the procedures of protocol Arm 2 are performed and, when done, workflow continues at the "Completed Therapy" scenario step 324.

After step 324, workflow for all patients proceeds to condition_step "ER+ or PR+" step 330. If a patient is neither estrogen-receptor positive nor progesterone-receptor positive, then the patient proceeds to a "CALGB 49802 long-term follow-up" sub-guideline object step 332. If a patient is either estrogen-receptor positive or progesterone-receptor positive, then the patient instead proceeds to a "Post-menopausal?" condition_step object 334. If the patient is post-menopausal, then the patient proceeds to a "Begin Tamoxifen" step 336, and thereafter to the long-term follow-up sub-guideline 332.

If in step 334, the patient is not post-menopausal, then workflow proceeds to a "Consider Tamoxifen" choice_step object 338. In this step, the physician using clinical judgment determines whether the patient should be given Tamoxifen. If so (choice object 340), then the patient continues to the "Begin Tamoxifen" step object 336. If not (choice object 342), then workflow proceeds directly to the long-term follow-up sub-guideline object 332. It will be appreciated that the graph 310 is only one example of a graph that can be created in different embodiments to describe the same overall protocol schema. It will also be appreciated that the library of object classes 312 could be changed to a different library of object classes, while still being oriented to protocol-directed clinical studies.

Figure 4:
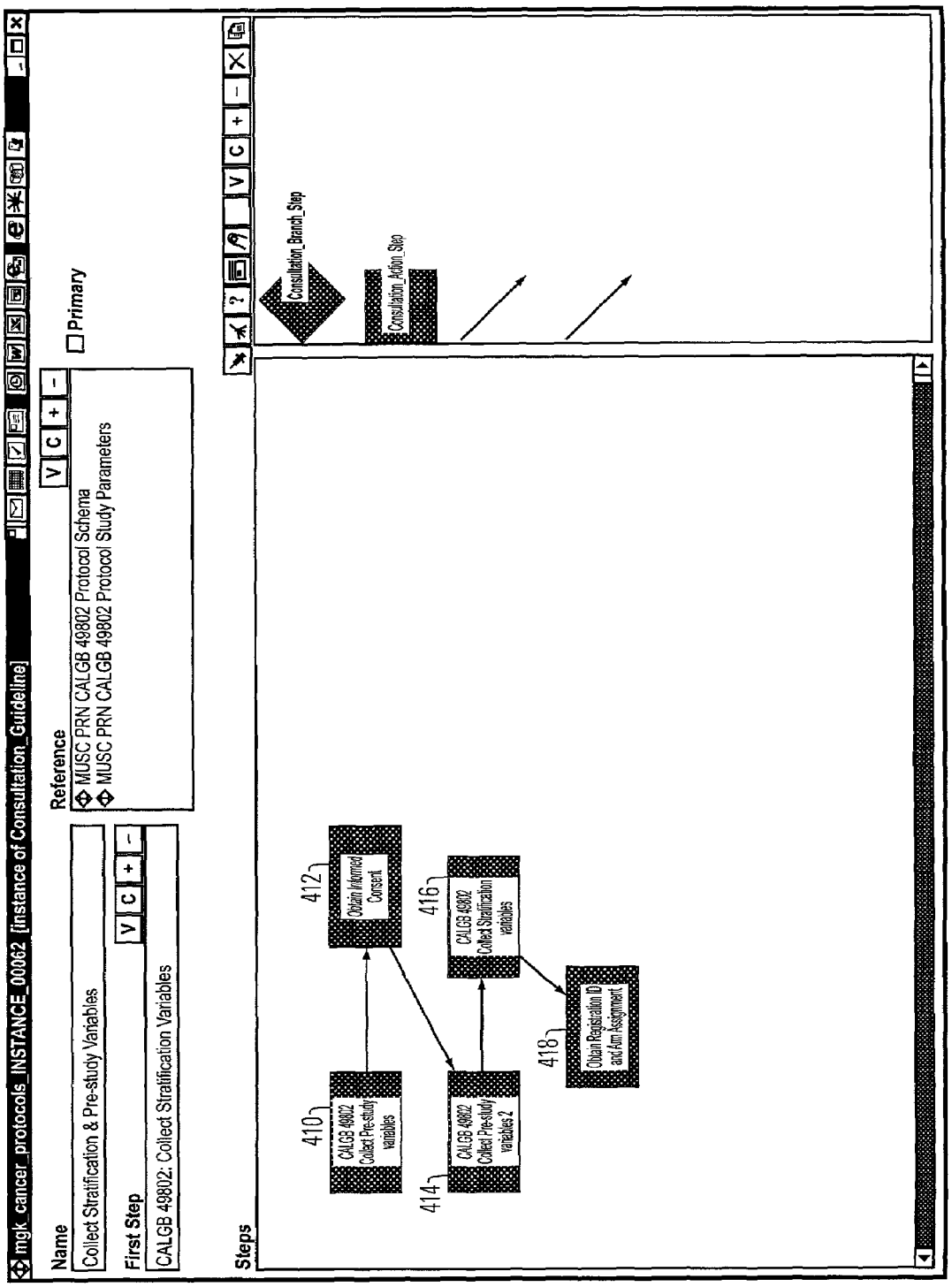

FIG. 4 is a screen shot showing the result of "drilling down" on the "Consent & Enroll" step 314 (FIG. 3). As can be seen, FIG. 4 contains a sub-graph (which is also considered herein to be a "graph" in its own right) 410. The Consent &

Enroll step 314 also contains certain text fields illustrated in FIG. 4 and not important for an understanding of the invention.

As can be seen, graph 410 begins with a "collect pre-study variables 1" step object 410, in which the clinician is instructed to obtain certain patient medical information that does not require informed consent. Step 412 is an "obtain informed consent" step, which includes a data management task instructing the clinician to present the study informed consent form to the patient and to request the patient's signature. In another embodiment, the step 412 might include a sub-graph which instructs the clinician to present the informed consent form, and if it is not signed and returned immediately, then to schedule follow-up reminder telephone calls at future dates until the patient returns a signed form or declines to participate.

After informed consent is obtained, the sub-graph 410 continues at step object 414, "collect pre-study variable 2". This step instructs the clinician to obtain certain additional patient medical information required for eligibility determination. If the patient is eligible for the study and wishes to participate, then the flow continues at step object 416, "collect stratification variables". The flow then continues at step 418, "obtain registration I.D. and Arm assignment" which effectively enrolls the patient in the trial.

FIG. 5 is a detail of the "Collect Stratification Variables" step 416 (FIG. 4). As can be seen, it contains a number of text fields, as well as four items of information that the clinician is to collect about the subject patient. When the clinical site protocol management software reaches this stage in the workflow, it will ask the clinician to obtain these items of information about the current patient and to record them for subsequent use in the protocol. The details of the "Collect pre-study variables" 1 and 2 steps 410 and 414 (FIG. 4) are analogous, except of course the specific tasks listed are different.

Figure 6:
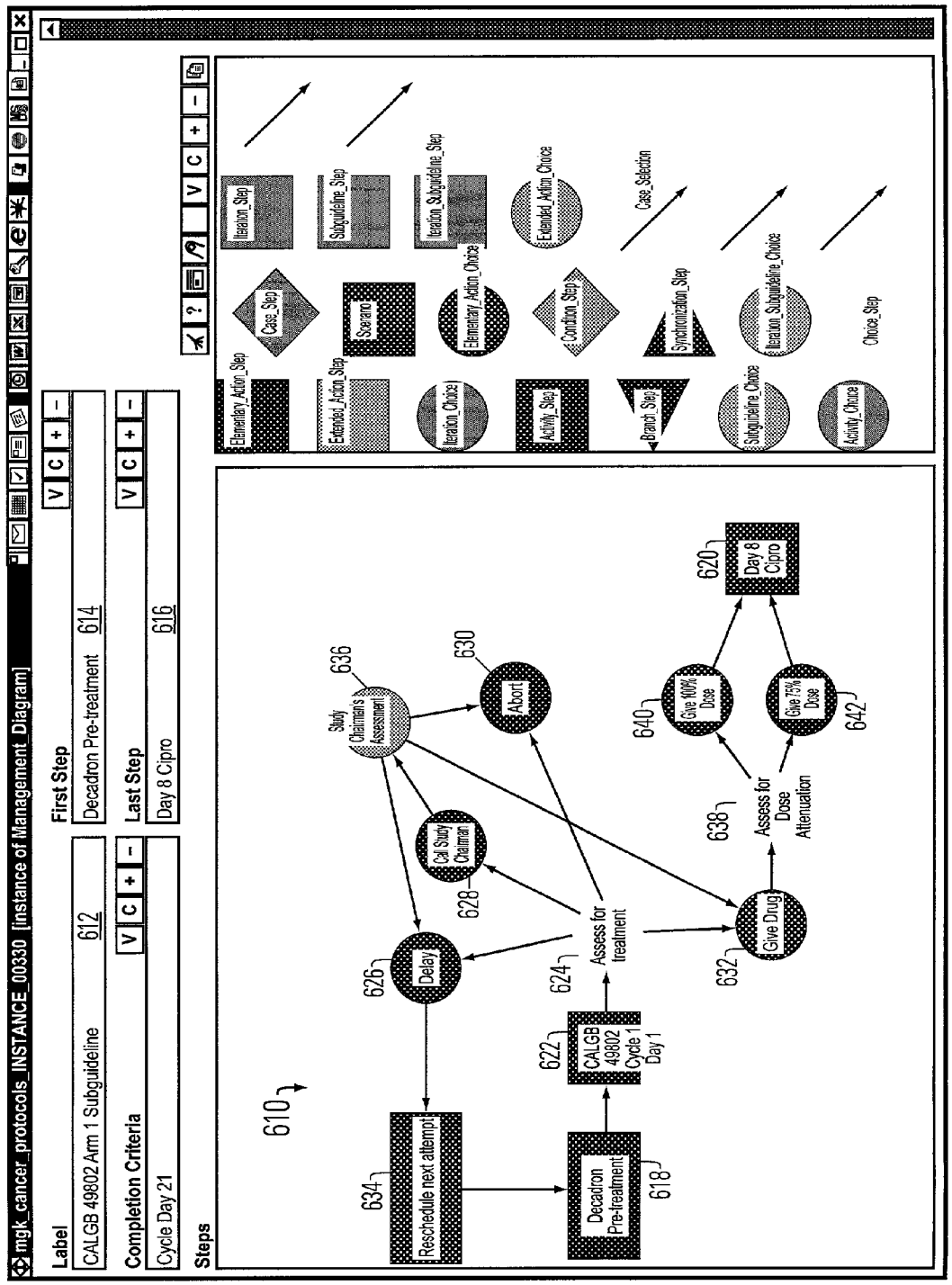

FIG. 6 is a detail of the "CALGB 49802 Arm 1" sub-guideline 332 (FIG. 3). As in FIG. 4, FIG. 6 includes a sub-graph (graph 610) and some additional information fields 612. The additional information fields 612 include, among other things, an indication 614 of the first step 618 in the graph, and an indication 616 of the last step 620 of the graph.

Referring to graph 610, the arm 1 sub-guideline begins with a "Decadron pre-treatment" step object 618. The process continues at a "Cycle 1; Day 1" object 622 followed by a choice_object 624 for "Assess for treatment." The clinician may make one of several choices during step 624 including a step of delaying (choice object 626); a step of calling the study chairman (choice object 628); a step of aborting the current patient (choice object 630); or a step of administering the drug under study (choice object 632). If the clinician chooses to delay (object 626), then the patient continues with a "Reschedule next attempt" step 634, followed by another "Decadron pre-treatment" step 618 at a future visit. If in step 624 the clinician chooses to call the study chairman (object 628), then workflow proceeds to choose_step object 636, in which the study chair makes an assessment. The study chair can choose either the delay object 626, the "Give Drug" object 632, or the "Abort" object 630.

If either the clinician (in object 624) or the study chair (in object 636) chooses to proceed with the "Give Drug" object 632, then workflow proceeds to choice_step object 638 at which the clinician assesses the patient for dose attenuation. In this step, the clinician may choose to give 100% dose (choice object 640) or to give 75% dose (choice object 642). In either case, after dosing, the clinician then performs "Day 8 Cipro" step object 620. That is, on the $8^{th}$ day, the patient begins a course of Ciprofloxacin (an antibiotic).

Without describing the objects in the graph 610 individually, it will be understood that many of these objects either are themselves specific tasks, or contain task lists which are associated with the particular step, visit or decision represented by the object.

Figure 7:
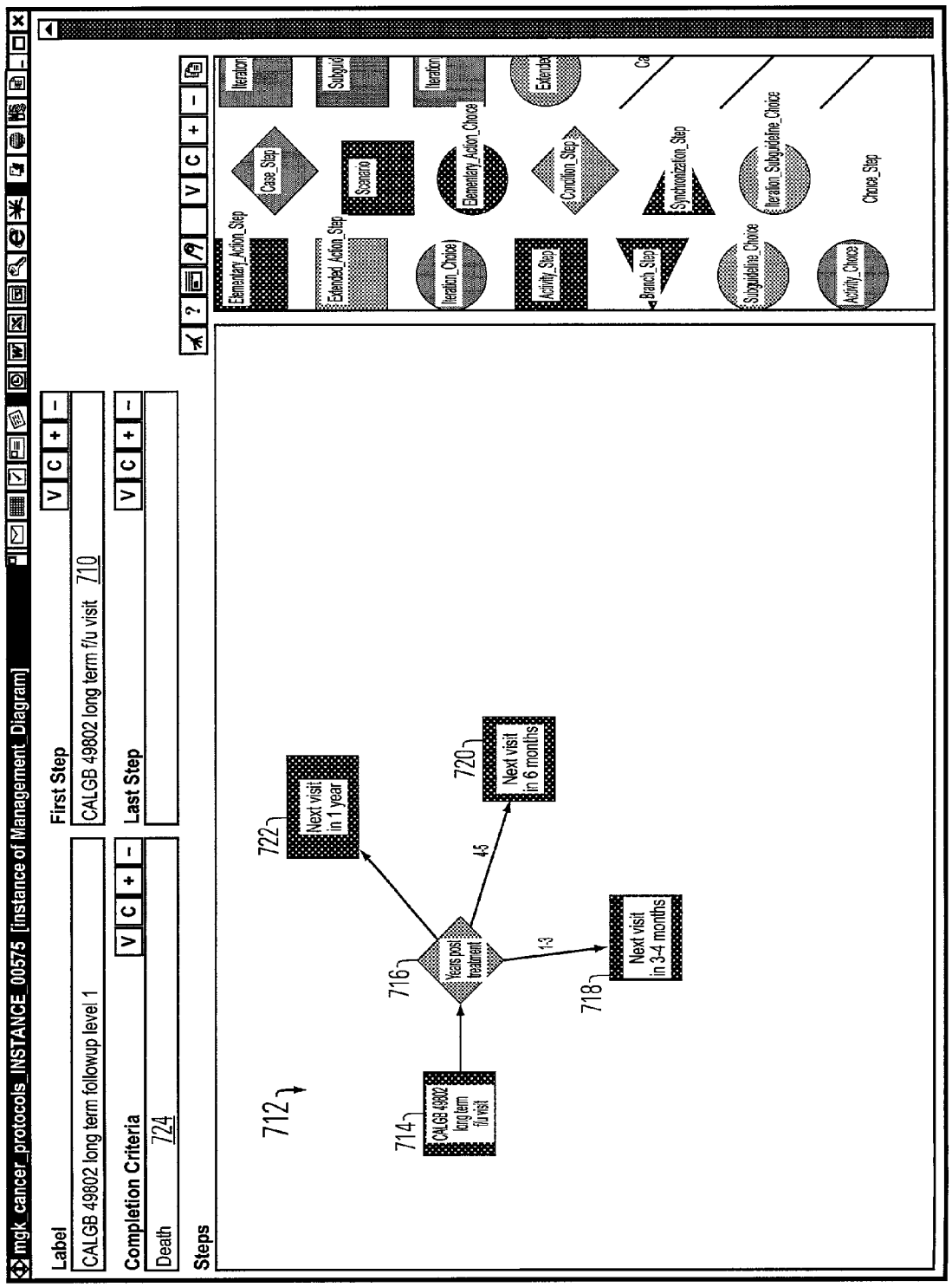

FIG. 7 is a detail of the long term follow-up object 332 (FIG. 3). As mentioned in field 710, the first step in the sub-graph 712 of this object is a long term follow-up visit scenario visit object 714. That is, the sub-guideline illustrated in graph 712 is executed on each of the patient's long-term follow-up visits. As indicated in field 724, the long term follow-up step 332 (FIG. 3) continues until the patient dies.

Object 716 is a case_object which is dependent upon the patient's number of years post-treatment. If the patient is 1-3 years post-treatment, then the patient proceeds to step object 718, which among other things, schedules the next visit in 3-4 months. If the patient is 4-5 years post-treatment, then the patient proceeds to step object 720, which among other things, schedules the next patient visit in 6 months. If the patient is more than 5 years post-treatment, then the patient proceeds to step object 722, which among other things, schedules the next visit in one year. Accordingly, it can be seen that in the sub-guideline 712, different tasks are performed if the patient is less than 3 years out from therapy, 4-5 out from therapy, or more than 5 years out from therapy. Beneath each of the step objects 718, 720 and 722 are additional workflow tasks that the clinician is required to perform at the current visit.

Figure 8:
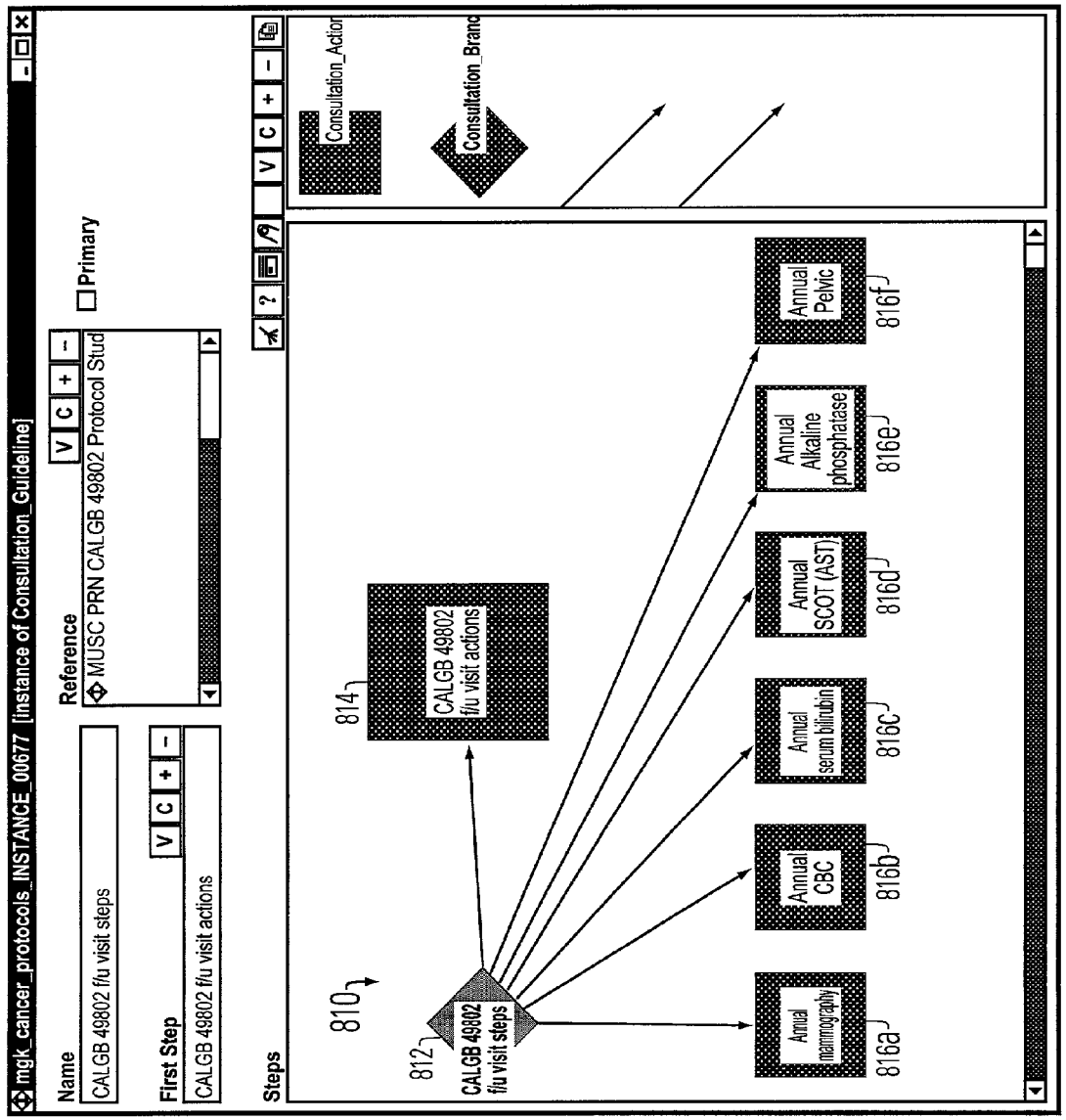

FIG. 8 is an example detail of one of the objects 718, 720 or 722 (FIG. 7). It includes a graph 810 which begins with a CALGB 49802 flu visit steps" consultation_branch object 812, followed by seven elementary_action objects 814 and 816a-f (collectively 816). Each of the consultation_action objects 814 and 816 includes a number of workflow tasks not shown in the figures. It can be seen from the names of the objects, however, that the workflow tasks under object 814 are to be performed at every follow-up visit, whereas the workflow tasks under objects 816 are to be performed only annually.

Figure 27:
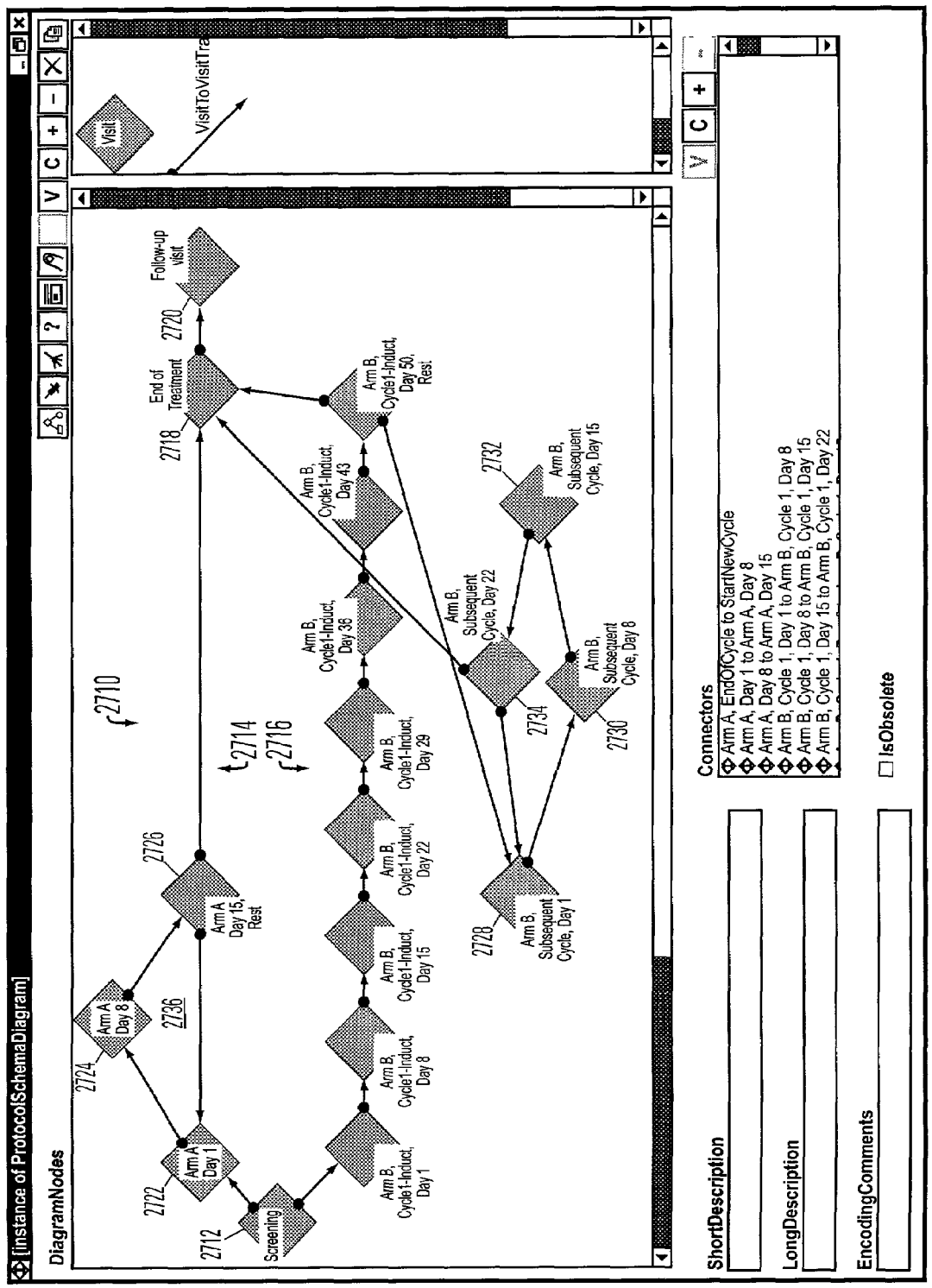
FIGS. 27-33 are additional screen shots produced by Protégé 2000, illustrating parts of an iCP class structure.

FIGS. 27-33 are screen shots of portions of yet another example iCP database, created and displayed by Protégé 2000 as an authoring tool. FIG. 27 illustrates the protocol schema 2710. It comprises a plurality of Visit objects (indicated by the diamonds), and a plurality of VisitToVisitTransition objects, indicated by arrows. The first Visit object 2712 in this example calls for certain patient screening steps. Following step 2712, the protocol schema 2710 divides into two separate "arms" referred to as Arm A and Arm B 2714 and 2716, respectively. The two arms rejoin at Visit object 2718, entitled "end of treatment." Following Visit object 2718 is another Visit object 2720, entitled "follow-up visit." In addition, within Arm A 2714, there are three Visit objects 2722, 2724 and 2726 which form a "cycle" 2736. That is, progress proceeds from object 2722 to object 2724, and then on to object 2726, and then conditionally back to object 2722 for one or more additional repetitions of the sequence. Alternatively, progress from Visit object 2726 can proceed to the "end of treatment" Visit object 2718. Arm B 2716 includes a cycle as well, consisting of Visit objects 2728, 2730, 2732 and 2734.

Figure 28:
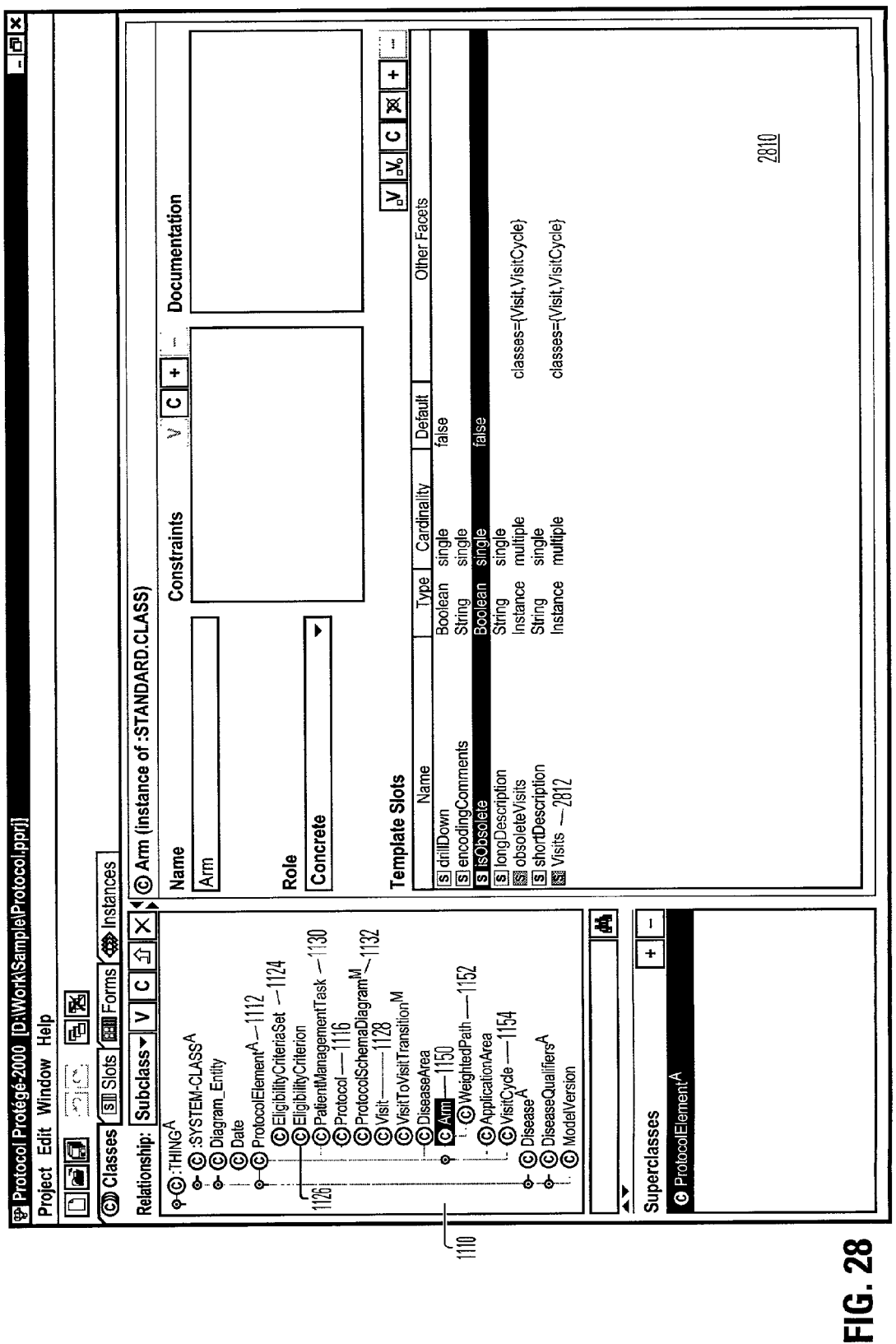
Figure 29:

The class structure in FIG. 11 includes three additional classes worthy of note here: Arm class 1150, WeightedPath class 1152, and VisitCycle class 1154. FIG. 28 illustrates in the right-hand pane 2810 the slots defined in the protocol meta-model for Arm class 1150. In particular, it can be seen that in slot 2812 and Arm object can include multiple instances of Visit objects and VisitCycle objects. FIG. 29 illustrates the contents of the Arm A instance of Arm object 2710. In the "visits" window, it can be seen that the object points to each of the Visit objects in Arm A 2710 in the protocol schema of FIG. 27, including the Visit objects 2712, 2718 and 2720 which are all common with Arm B.

Figure 30:
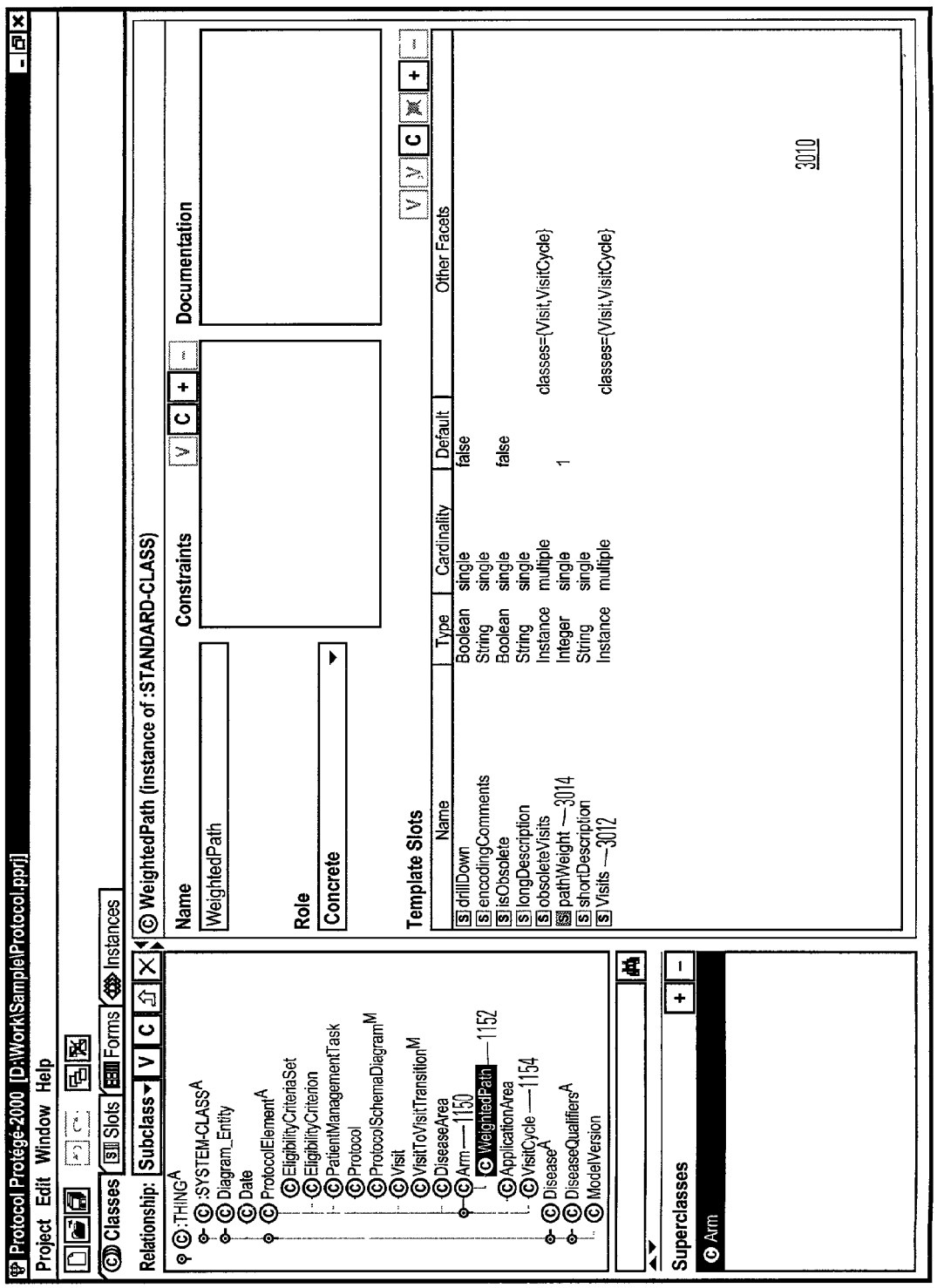
Figure 31:

FIG. 30 illustrates in the right hand pane 3010 the slots defined in the protocol meta-model for the class Weighted-Path 1152. It can be seen that the WeightedPath class 1152 includes a slot 3012 for Visits, like the Arm class 1150; but also includes a slot 3014 for a pathWeight value. FIG. 31 illustrates an instance of a WeightedPath object 3110, again corresponding to Arm A 2714 in the protocol schema of FIG. 27. As can be seen, WeightedPath object 3110 includes the Visits 2712, 2718 and 2720, and also includes the Visits 2722, 2724 and 2726 as a single VisitCycle object 2736. Weighted-Path object 3110 also includes the integer "1" as the PathWeight.

Figure 32:
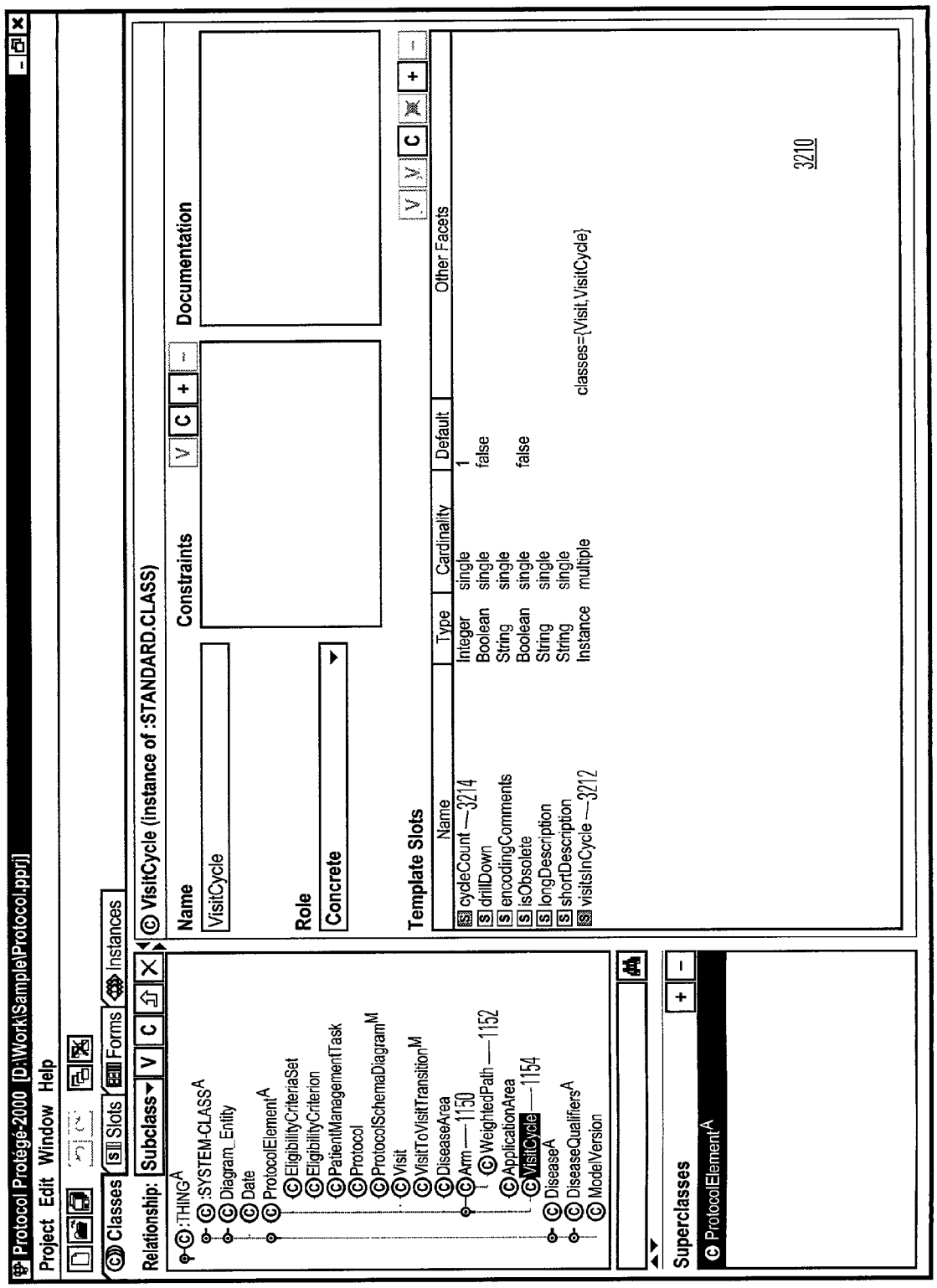
Figure 33:

FIG. 32 illustrates in the right-hand pane 3210 the slots defined in the protocol meta-model for the class 1154, Visit-Cycle. Of particular note is that it includes a slot entitled visitsInCycle 3212, for identifying multiple instances of Visit or VisitCycle class objects. It also includes a slot 3214 for a cycleCount value, indicating the number of times a patient is expected to traverse the cycle. FIG. 33 is a sample instance for VisitCycle 2736 of FIG. 27. As can be seen, it includes the three Visit objects 2722, 2724 and 2726, and it also includes a cycleCount of three.

Because of the ability to support domain-independent PSMs, the iCPs of the embodiments described herein enable automation of the entire trials process from protocol authoring to database lock. For example, the iCP is used to create multiple trial management tools, including electronic case report forms, data validation logic, trial performance metrics, patient diaries and document management reports. The iCP data structures can be used by multiple tools to ensure that the tool performs in strict compliance with the clinical protocol requirements. For example, an accrual simulation tool can be implemented as a domain-independent PSM. Similarly, an embodiment can also include a PSM that clinical sites can use to simulate their own accrual in advance of signing on to perform a given clinical trial. A single PSM is used to simulate accrual into a variety of studies, because the patient eligibility criteria are all identified in a predetermined format in the iCP for each study. Another PSM helps clinical sites identify likely patients for a given clinical trial. Yet another PSM guides clinicians through the visit-specific workflow tasks for each given patient as required by the protocol. The behavior of all these tools is guaranteed to be consistent with the protocol even as it evolves and changes because they all use the same iCP. The tools can also be incorporated into a library that can be re-used for the next relevant trial, thus permitting knowledge to be transferred across trials rather than being re-invented each time.

Figure 9:
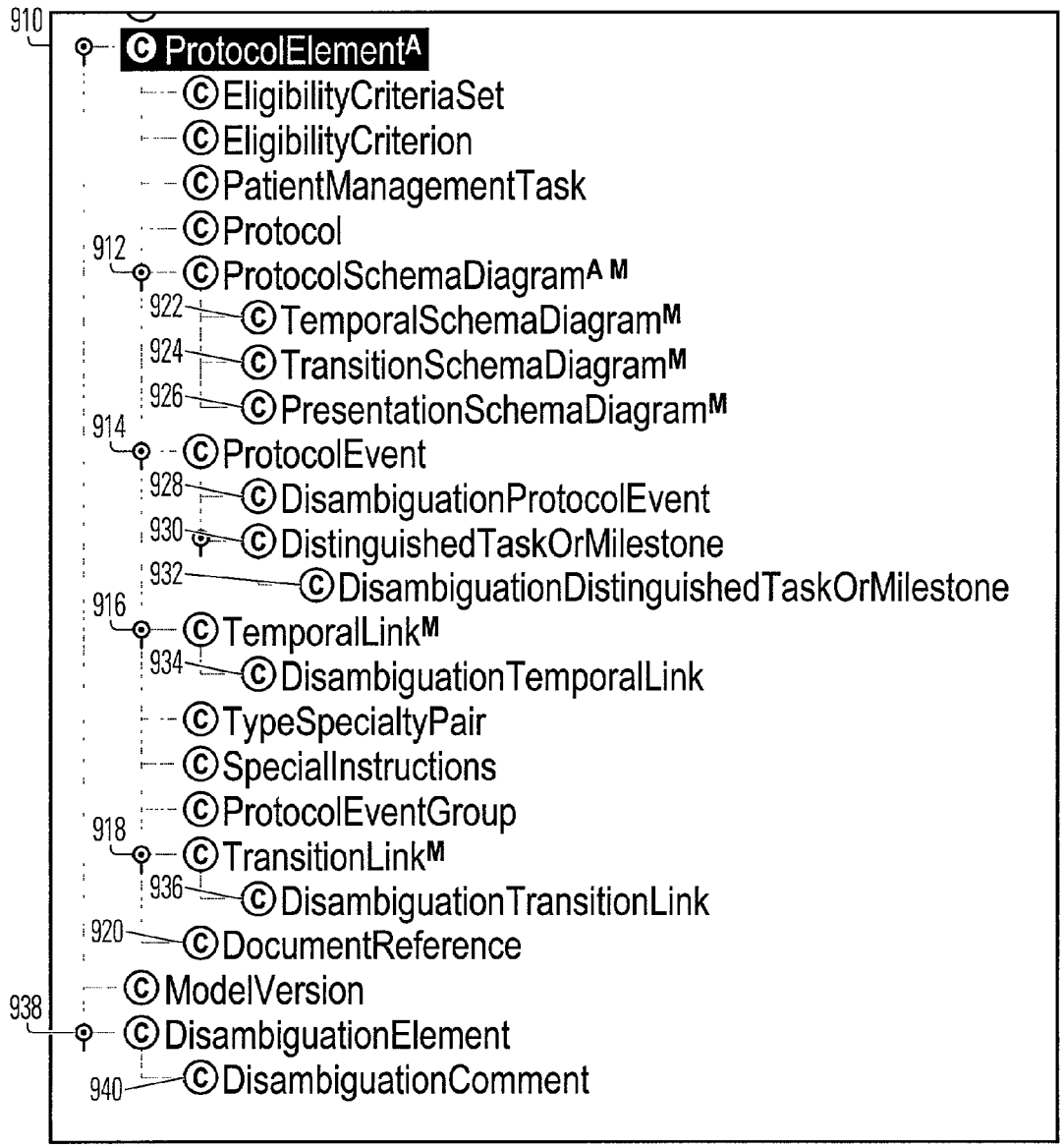
FIG. 9 illustrates the class structure for another embodiment of the invention.

It will be appreciated that a wide variety of different protocol meta-models (class structures) can be used for the purpose of detecting operational uncertainties during the encoding of a text-based clinical trial protocol into machine-readable form. FIG. 9 illustrates the class structure for yet another embodiment of the invention, starting with the superclass ProtocolElement 910. It can be seen that the class structure of FIG. 9 includes, among other things, a subclass 912 for "ProtocolSchemaDiagram", a subclass 914 for "ProtocolEvent", a subclass 916 for "TemporalLink", a subclass 918 for "TransitionLink", and a subclass 920 for "DocumentReference". The class ProtocolSchemaDiagram 912 includes three subclasses respectively entitled "TemporalSchemaDiagram" 922, "TransitionSchemaDiagram" 924, and "PresentationSchemaDiagram" 926. ProtocolEvent class 914 includes two subclasses respectively entitled "DisambiguationProtocolEvent" 928 and "DistinguishedTaskOrMilestone" 930. DistinguishedTaskOrMilestone subclass 930 includes a further subclass "DisambiguationDistinguishedTaskOrMilestone" 932. TemporalLink class 916 includes a "DisambiguationTemporalLink" subclass 934, and TransitionLink class 918 includes a subclass "DisambiguationTransitionLink" 936. The structure also includes a superclass "DisambiguationElement" 938, which includes its own "DisambiguationComment" subclass 940. Relevant ones of these classes and subclasses are discussed hereinafter.

FIG. 10 illustrates the definition for instances of superclass ProtocolElement 910. All subclasses below the ProtocolElement superclass 910 inherit the template slots illustrated in FIG. 10. Of particular note are the slots 1012 and 1014 for containing long and short descriptions of instances of each subclass, and slot 1010, "disambiguationComments", for identifying one or more "disambiguationComment" objects to be associated with the protocol event. Thus every kind of object instantiated from a subclass below the ProtocolElement superclass 910 can contain or identify a comment, prepared by the encoder, regarding an ambiguity or uncertainty in the protocol. The slot 1010 has multiple cardinality, so an object instantiated from any of the ProtocolElement subclasses can have associated therewith more than one DisambiguationComment object. It can also have associated therewith no disambiguation comments at all, a situation which indicates that no operational uncertainties have been identified and associated with the particular object. Note that whereas the present embodiment encodes operational uncertainties in separate objects pointed to by the ProtocolElement object to which they relate, other embodiments can encode operational uncertainties directly in the associated ProtocolElement object, for example in one or more text fields.

Figure 13:
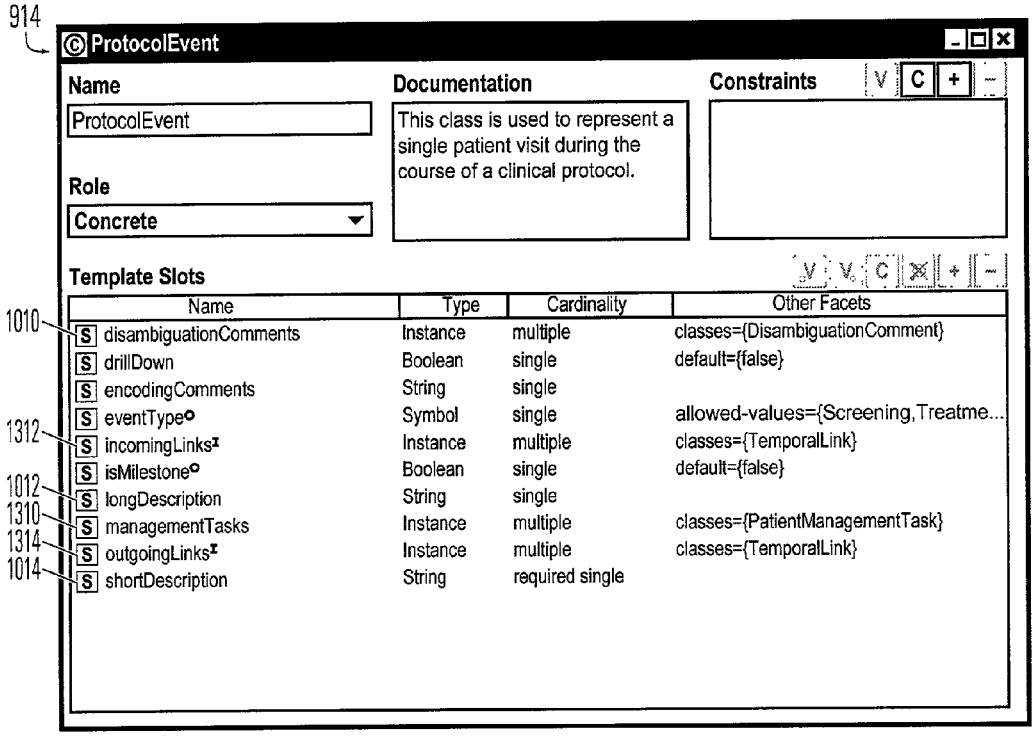

FIG. 13 illustrates a class definition for the "ProtocolEvent" class 914. It can be seen that in addition to the disambiguationComments slot 1010, the short description slot 1014 and the long description slot 1012 inherited from the parent ProtocolElement class 910, the class ProtocolEvent 914 also defines a slot 1310 for "ManagementTask", a slot 1312 for "incomingLinks", and a slot 1314 for "outgoingLinks". The incomingLinks slot 1312 and outgoingLinks slot 1314 point to objects of class TemporalLink 916. When the protocol schema is displayed graphically in a temporal schema diagram, objects of ProtocolEvent class 914 will be displayed as diamonds, and the incoming and outgoing TemporalLink objects will be displayed as arrows directed toward or away from the diamonds, respectively. The incomingLinks and outgoingLinks slots 1312 and 1314 are of multiple cardinality, which means that each ProtocolEvent object can have zero, one or more incoming and outgoing temporal links to other ProtocolEvent objects.

As illustrated in FIG. 9, the ProtocolEvent class 914 includes a DisambiguationProtocolEvent subclass 928. The subclass 928 has the identical definition as the ProtocolEvent class 914, and that definition will not be repeated here. The DisambiguationProtocolEvent subclass 928 exists only because when Protégé 2000 is used to display the ProtocolSchemaDiagram graphically in a way that shows disambiguation, a separate subclass is required in order to have an object of ProtocolEvent class 914 appear in a different color depending on the presence or absence of any associated disambiguation comments. In another embodiment, such a separate subclass may not be required.

FIG. 14 illustrates an example instance of DisambiguationProtocolEvent class 928. An instance of ProtocolEvent class 914 would appear similar. It can be seen that the instance of FIG. 14, in addition to a short description, a long description, identification of one incoming temporal link and identification of six ManagementTask objects, the instance also identifies a DisambiguationComment object 1410, called "Inconsistent tasks in tx plan and assessment." This is a pointer to an object of DisambiguationComment class 940 (FIG. 9), which describes the issue more completely.

FIG. 15 illustrates the class definition for the "TemporalLink" class 916. As with DisambiguationProtocolEvent subclass 928, TemporalLink class 916 includes a DisambiguationTemporalLink subclass 934 which has the same definition as the TemporalLink class 916. It exists in the class structure of FIG. 9 only to facilitate the displaying of an object of TemporalLink class 916 in a different color depending on the presence or absence of one or more disambiguation comments associated with the TemporalLink object. It can be seen from FIG. 15 that in addition to the slots for disambiguationComments 1010, short description 1014 and long description 1012, the definition of a TemporalLink object also includes template slots 1510 for "first_object" and 1512 for "second_object". These slots are to be filled with single instances of objects of ProtocolEvent class 914, and represent the anchoring and target protocol events for a TemporalLink object.

The class definition of a TemporalLink object also includes template slots 1516, 1518 and 1520, for "minimum relative offset", "maximum relative offset" and "preferred relative offset", respectively. It also includes an "offset units" template slot 1522, which is provided to allow the encoder to specify the time units with which the minimum, maximum and preferred relative offsets are being identified. The minimum, maximum and preferred relative offset slots, together with the offset units slot 1520, allow the encoder to encode into the iCP any constraints that the text-based clinical trial protocol calls for regarding the timing of the ProtocolEvent object specified in the second_object slot 1512 relative to the timing of the ProtocolEvent object specified in the first_object slot 1510. Objects instantiated according to be TemporalLink class 916, therefore, are examples of what is sometimes referred to herein as a temporal constraint object.

As with the other embodiments described herein, temporal constraint objects in various embodiments can instead or additionally be described in probabilistic terms, or can instead be specified with only a single offset. As yet another alternative, temporal constraint objects in various embodiments can be specified with only partially defined ranges, such as a minimum time without a maximum time, or as a maximum time without a minimum time. As previously explained, temporal constraints are a frequent area for uncertainty in many text-based clinical trial protocols, and a class structure which requires an analyst to locate this information in the text-based protocol and ensure its consistency throughout the protocol, is tremendously beneficial in helping to identify operational uncertainties in the protocol.

As used herein, "operational uncertainties" include parameters that are either specified inconsistently in the text-based protocol, or specified only vaguely, or omitted altogether. Some parameters in a clinical trial protocol are left uncertain intentionally, and a well-designed database model will accommodate this level of uncertainty. For example, the temporal constraint from one protocol event to another may be specified in the text-based protocol as a permissible range of time periods, or as minimum, maximum and base time periods, or as a probability function. These may constitute "operational uncertainties" with respect to a simple database model that requires entry of only a single precise time period, but not with respect to more sophisticated database models that allow entry of the temporal constraint parameters in the form provided in the text. As another example, protocol specifications that intentionally allow some discretion on the part of the physician, are not necessarily "operational uncertainties". Thus an uncertainty is not considered an "operational uncertainty" unless the protocol specifies the parameter either with unintentional ambiguity, or not at all, or with sufficient unintentional uncertainty that it cannot be encoded into the database without additional information from the provider of the protocol.

Figure 16:
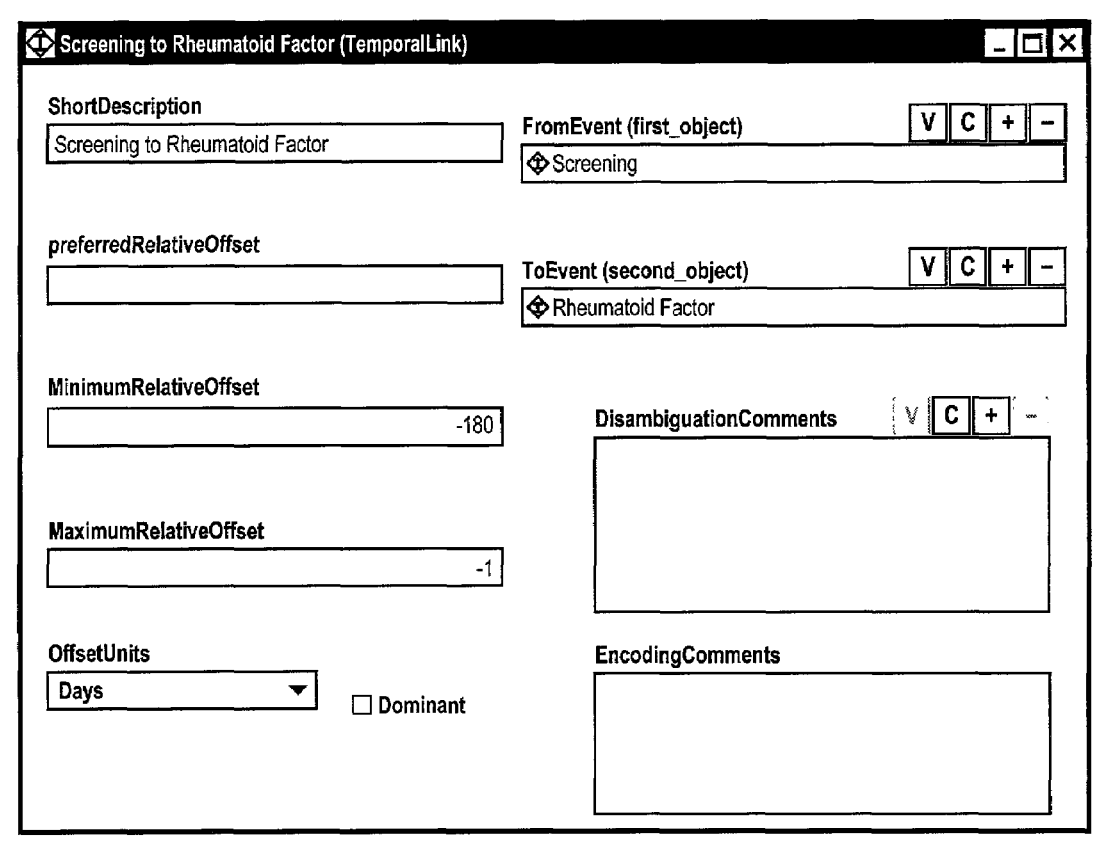

FIG. 16 illustrates an instance of TemporalLink class 916. It can be seen that this particular object specifies minimum and maximum numbers of days from the occurrence of a "screening" protocol event to the occurrence of a "rheumatoid factor" protocol event. In many TemporalLink objects the time periods specified will be positive, but in the object illustrated FIG. 16, the time periods specified are negative. This object therefore encodes a requirement in the text-based clinical trial protocol that a rheumatoid factor must have appeared within the range of days specified, before the screening visit.

Note that the time constraints that an analyst encodes into a TemporalLink object need not be between two ProtocolEvent objects which occur sequentially in the protocol workflow. This allows the analyst to encode temporal constraints specified in the text-based protocol such as, "visit 2 must occur within 5±1 day of visit 1, and visit 3 must occur within 10±1 day of visit 1." This kind of constraint, which is common in clinical trial protocols, can be encoded in the class structure of FIG. 9 by instantiating a first object of class TemporalLink, identifying the visit 1 ProtocolEvent object as the "first_object" and the visit 2 ProtocolEvent object as the "second_object"; and by instantiating a second object of class TemporalLink, identifying the visit 1 ProtocolEvent object as the "first_object" and the visit 3 ProtocolEvent object as the "second_object." Objects of TemporalLink class 916 therefore do not specify any sequence between ProtocolEvent objects, except perhaps by inference from allowable time periods as specified in different objects of the class. The "TransitionLink" class 918 (FIG. 9), and its associated DisambiguationTransitionLink subclass 936, are provided for encoding the sequence of protocol events. The definition (not shown) for TransitionLink class 918 includes slots for the originating and target ProtocolEvent objects, but does not include slots for temporal constraints. It will be appreciated that in other embodiments, classes (such as VisitToVisitTransition class of FIG. 22) which include both sequence information and temporal constraints can be defined.

FIG. 26 illustrates the class definition for DisambiguationComment class 940. It includes template slots that allow the analyst to summarize the operational uncertainty at issue, indicate specifically where it appears in the text-based protocol document, and indicate the analyst's view of the significance of the uncertainty and a recommendation for correction. Specifically, the definition includes among other things a slot 2610 in which the analyst identifies which section or sections of the text-based protocol contained the uncertainty, and a DocumentReference slot 2612 for providing more information about the location(s) of the uncertainty in the document. The definition also includes a slot 2614 for "impact type", in which the analyst selects a category of impact that a particular finding potentially can have on the protocol execution. The definition also includes an "issue" slot 2616, in which the analyst describes the issue that engendered the particular DisambiguationComment object. It also includes a "potential impact" slot 2618, in which the analyst describes the potential impact of the uncertainty on a clinical trial conducted according to the protocol, and a "recommendation" slot 2622, in which the analyst describes a recommendation for correcting the uncertainty. The definition also includes a "protocol text" slot 2620 for quoting the relevant snippet of text from the text-based protocol document, as well as a "severity level" slot 2624. "Impact Type" slot 2614 can include values such as Safety, Efficacy-primary, Efficacy-secondary, Administrative, Regulatory, Accrual, Delay in IRB approval, Excessive site queries, and Other.

The severity level slot 2624 allows the analyst to classify a particular finding either as Level One or Level Two, depending on the potential significance of the finding and its risk in impacting the study. A Level One finding identifies an inconsistency or clarification issue that could result in a deleterious effect on the study and its results. An issue is classified as Level One if the inconsistency has a reasonable probability of resulting in missing or incomplete study data, unevaluable subject(s), inconsistent study conduct, protocol non-compliance, protocol violation, or undesirable variability across study subjects. Correcting a Level One inconsistency is likely to have a direct positive impact on both the validity and cost of the study. A Level Two finding, on the other hand, identifies an inconsistency or clarification issue that has been highlighted as a candidate for amendment in order to increase the clarity of the protocol. Amending a Level Two inconsistency could significantly reduce the frequency of clarification requests from sites and investigators, thus having a positive impact on the overall study-management cost of the study. It will be appreciated that other embodiments can provide other definitions for the severity level slot, and indeed can define the slots for a DisambiguationComment object quite differently than what is illustrated in FIG. 26.

Figure 34:
FIGS. 34 and 35 illustrate an example object instantiated according to the DisambiguationComment class in the class structure of FIG. 9.
Figure 35:

FIG. 34 illustrates a sample instance of a DisambiguationComment object. FIG. 35 illustrates a sample instance of another DisambiguationComment object, this one instantiated according to a class definition which differs slightly from that of FIG. 26. In particular, instead of identifying locations in the text-based protocol using a DocumentReference object, the object of FIG. 35 incorporates many of the fields of a DocumentReference object directly into the DisambiguationComment object. This and other variations apparent to a person of ordinary skill still incorporate aspects of the invention.

Figure 36:
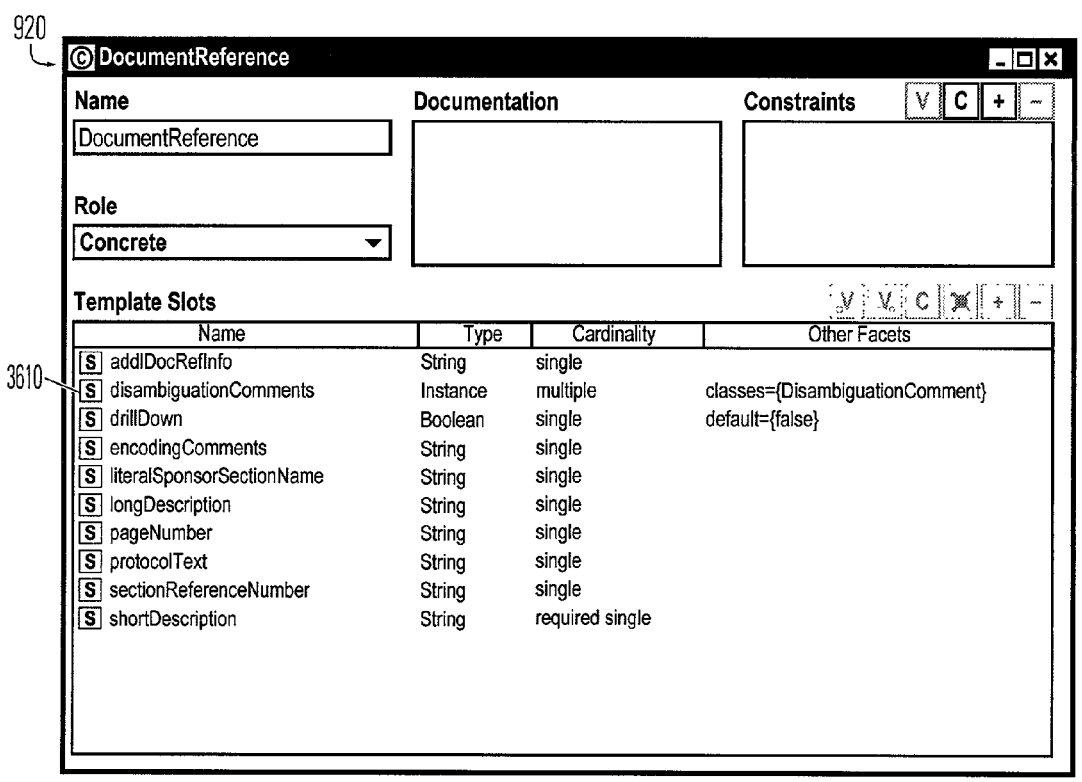

FIG. 36 illustrates a class definition for the DocumentReference class 920 (FIG. 9). It includes a slot 3610 for pointing to one or more DisambiguationComment objects, as well as various text slots in which the analyst enters such details as a literal sponsor section named, short and long descriptions, a page number, a section reference number, and text from the text-based protocol. As mentioned, other embodiments can include all this information directly in a DisambiguationComment object, or different information entirely. FIG. 37 illustrates a sample instance of a DocumentReference object.

As mentioned above, the class structure illustrated in FIG. 9 defines three types of protocol schema diagrams. When it is desired to create a graphical-visual display of a protocol schema encoded into an iCP, the user first selects which of the three types of diagrams to display. As used herein, "displaying" includes displaying on a monitor, printing on paper, and any other kind of rendering, as long as it is human-perceptible. A TransitionSchemaDiagram object (subclass 924) shows the sequence of protocol events but does not specify any temporal constraints. Transition schema diagrams appear similarly to those illustrated in FIGS. 6, 7, 8, 25 and 27. A TemporalSchemaDiagram object (subclass 922) appears similar to a transition schema diagram, except that the arrows represent temporal constraints rather than protocol event sequence. A PresentationSchemaDiagram object (subclass 926) appears the same as a temporal schema diagram, except that graphical objects appearing on the diagram appear different in some human-perceptible way depending on whether one or more DisambiguationComment objects have been associated with them. They also appear differently in a different human-perceptible way depending on certain other attributes, such as whether or not the object is considered a "milestone" protocol event. In the embodiment presently being described, an object appears on the display in a different color depending on whether one or more DisambiguationComment objects are associated with it, and appears in a different shape depending on whether the object is a milestone object. In other embodiments, the human perceptible differentiators can include other kinds visual indications, such as heavy lines, a border, shading, a modified shape, blinking, and so on, or even an audible indication, such as the playing of a sound when the mouse pointer passes over an object having a disambiguation comment associated therewith.

In the presently describe embodiment, a disambiguation object or comment contained only indirectly within a graphical object is considered nevertheless to be associated with the graphical object. For example, if a disambiguation comment has been associated with a task object identified by a ProtocolEvent object, then the disambiguation comment is considered in this embodiment to be also associated with the ProtocolEvent object. The ProtocolEvent object therefore will be displayed in a different color when copied into a presentation schema diagram. Another embodiment might provide a different way to reveal the presence of a disambiguation comment that is associated with a graphical object only indirectly.

Figure 38:
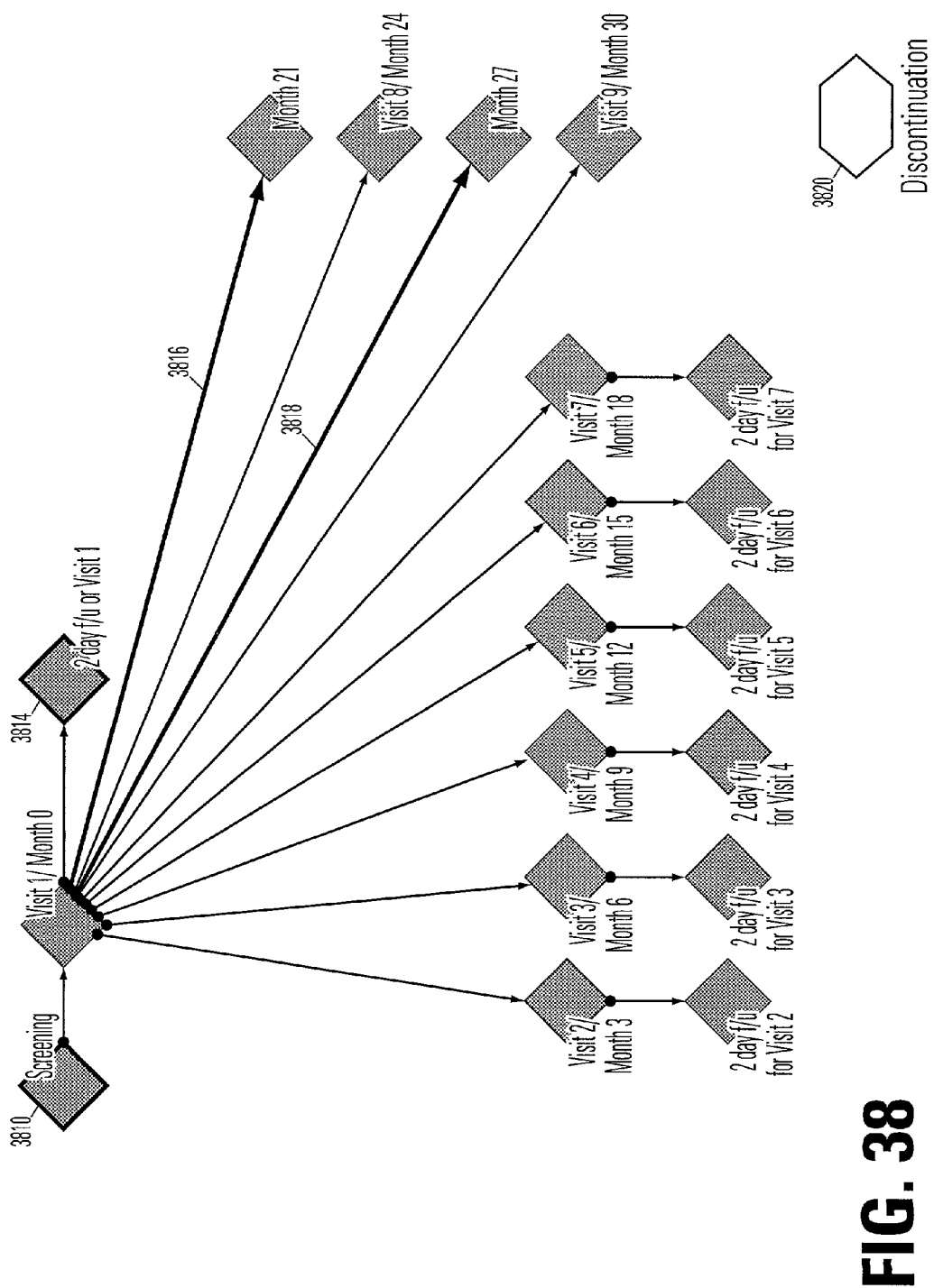
FIG. 38 illustrates a sample presentation schema diagram.

FIG. 38 illustrates a sample presentation schema diagram displaying ProtocolEvent objects (diamonds) and temporal constraint objects (arrows). Clicking on any object in the diagram displays the underlying details about object. For purposes of the present patent application, all objects in FIG. 38 are illustrated in black and white. In actual display, all of the ProtocolEvent objects are displayed in green except for the objects 3810 and 3814, which are displayed in red. Similarly, all of the TemporalLink objects in actual display are displayed in black, except for the objects 3816 and 3818, which are displayed in red. The red objects indicate to the viewer the presence of at least one disambiguation comment associated with these objects. In addition, ProtocolEvent object 3820 in actual display appears aquamarine in color and hexagonal in shape, indicating that it is a ProtocolEvent object of DistinguishedTaskOrMilestone subclass 930 (FIG. 9), rather than another kind of ProtocolEvent object. If there were a disambiguation comment associated with ProtocolEvent object 3820, then it would appear in the display as a red hexagon (or in yet another color).

Note that ProtocolEvent object 3820 has no associated TemporalLink objects. This is entirely possible in a particular clinical trial protocol, and indicates that the particular protocol event could, according to the protocol, occur at any time.

FIG. 1 is a flowchart illustrating the tasks that an analyzer of a text-based clinical trial protocol can perform in order to help identify operational uncertainties in the protocol. It will be appreciated that many of the steps illustrated in the flow chart of FIG. 1 can be performed in parallel or in a different sequence without affecting the functions achieved. In the step 110, an analyst receives a text-based clinical trial protocol for analysis. As used herein, a text-based protocol can be provided either in paper form or in electronic form (such as in a word processing document), or both. In the step 112, the analyst instantiates objects of class ProtocolEvent corresponding to each event that can take place according to the text-based protocol. In the Protégé 2000 knowledge acquisition tool, this can be accomplished by dragging ProtocolEvent objects from a palette into a graphical representation of the protocol schema. In step 114, the analyst begins looping through all of the ProtocolEvent objects instantiated in step 112.

In step 116, the analyst fills in all of the slots of the current ProtocolEvent object based on the text-based protocol description. This may include filling in text fields of the ProtocolEvent object, instantiated and filling in other objects (such as ManagementTask objects) that are pointed to by the ProtocolEvent object, and locating in the text-based protocol all of the required information for completing these slots. The analyst "drills down" on the graphical protocol event object to enter the detailed tasks that are to be performed during the particular event.

When encoding at this level of formality, a checklist of editorial rules is applied to help uncover any inconsistencies. The particular, the encoding process drives the analyst to note visit and task details both in the study schema and in the body of the protocol. As each section of the protocol is examined in order to fill in details of the iCP, consistency rules are applied, and cross-section inconsistencies are also detected. Additional editorial rules are applied throughout, such as those examining the consistency of label assignments, missing protocol sections, inconsistent or undefined internal and external references, and undefined acronyms. Whenever an item is detected as an operational uncertainty (step 118), the analyst in step 120 instantiates a disambiguation object and associates it with the object in question. The analyst then fills in the description of the issue noted, as previously described with respect to FIGS. 34 and 35.

In step 121, the analyst determines whether there any more ProtocolEvent objects to be filled in. If so, then the analyst returns to step 114 to fill in the slots of the next object. If not, then in step 122, the analyst instantiates objects of class TemporalLink corresponding to each event-to-event temporal constraint required by the protocol. In step 124, the analyst loops through all the temporal constraints, and in step 126, the analyst fills in all the slots of the current TemporalLink object from the text-based protocol description. Of particular note, the analyst fills in the appropriate slots to indicate all temporal constraints required. Again, the rigor of this encoding process significantly enhances the analyst's ability to uncover operational uncertainties in the text-based protocol, especially but not exclusively with respect to temporal constraints.

In step 128, if the analyst is unable to complete one or more slots of the current TemporalLink object and because the information is vague, omitted or ambiguous in a text-based protocol, then in step 130, the analyst instantiates a disambiguation object, associates it with the subject slot or TemporalLink object, and fills in the description as previously described. In step 132, if there are any more temporal constraints to be encoded, the analyst returns to step 124 for filling in the slots of the next TemporalLink object. If there are no more temporal constraints to be encoded, then the analyst at this point can also optionally encoded other protocol objects, such as TransitionLink objects.

After the encoding process is complete, in step 134, a user can generate and display a presentation schema diagram from the resulting iCP, including objects which are colored red (for example) to indicate the presence of an associated DisambiguationComment object. In step 136, a user optionally can drill down on any of the red-colored objects, to any of the disambiguation objects which have been associated with the object appearing in the display in red.

The process in step 134 for creating a desired presentation schema diagram can be performed in a number of different ways. In the embodiments described herein, no separate tool is necessary for developing the temporal or transition schema diagram from other objects in an iCP because the knowledge acquisition tool that the analyst uses (for example in steps 112, 116, 122 and 126 (FIG. 1)) creates the TemporalSchemaDiagram objects and TransitionSchemaDiagram objects directly. The knowledge acquisition tool creates ProtocolEvent objects and TemporalLink objects automatically from a TemporalSchemaDiagram object as it is being formed, rather than creating the TemporalSchemaDiagram object from the ProtocolEvent and TemporalLink objects. But the ProtocolSchemaDiagram created by the knowledge acquisition tool is a temporal schema diagram, not a presentation schema diagram. As mentioned above, a temporal schema diagram does not show human-perceptible indications of the presence or absence of disambiguation objects.

Figure 39:
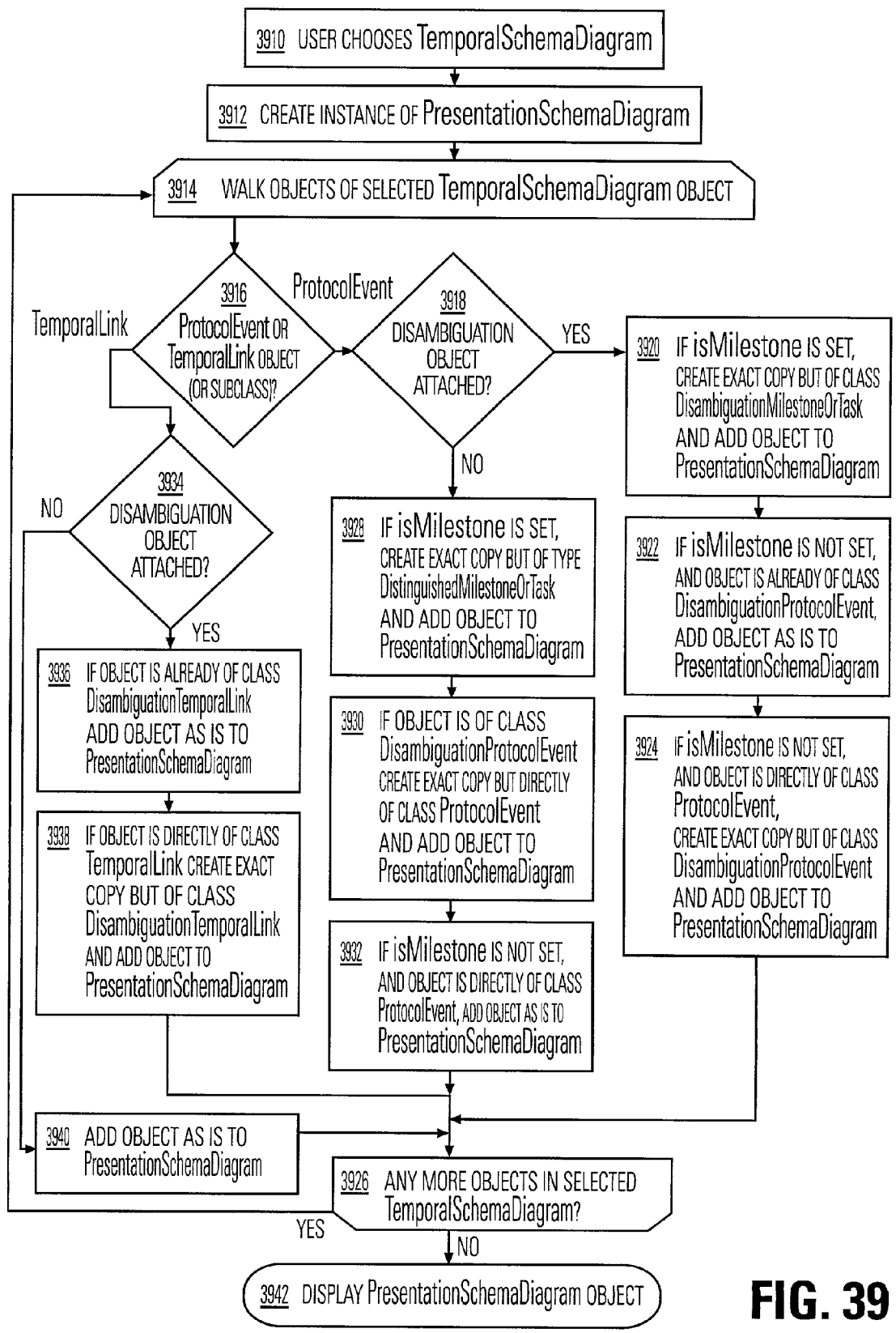
FIG. 39 is a flowchart for generating a presentation schema diagram from a temporal schema diagram.

FIG. 39 is a flowchart describing a Protégé 2000 problem solving tool which generates a presentation schema diagram from a temporal schema diagram so that such human-perceptible indications can be displayed. As with FIG. 1, many of the steps illustrated in the flow chart of FIG. 39 can be performed in parallel or in a different sequence without affecting the functions achieved.

Referring to FIG. 39, in step 3910, the user chooses a TemporalSchemaDiagram object from a selected iCP. In step 3912, the system creates a new instance of class PresentationSchemaDiagram. In step 3914, the system begins to walk the objects of the selected TemporalSchemaDiagram object. Any algorithm for traversing all of the nodes and connectors of a conventional graph can be used for walking the objects of the TemporalSchemaDiagram object. In step 3916, the system determines whether the current object is an instance of class ProtocolEvent (or any of its subclasses), or is an instance of class TemporalLink (or of any of its subclasses). If the object is an instance of class ProtocolEvent or one of its subclasses, then in step 3918, the system determines whether the object has associated therewith a disambiguation object. Again, in the present embodiment, such an association can be either direct or indirect. The system detects the absence of a disambiguation comment by detecting the absence of any pointers to DisambiguationComment objects, both in the ProtocolEvent object directly and in all objects contained, directly or indirectly, in the ProtocolEvent object. In another embodiment, absence of a disambiguation comment can be detected by reference to a separate Boolean slot in the object indicating whether or not a DisambiguationComment is associated with the object.

If the current ProtocolEvent object does have a disambiguation object attached, then in step 3920, the system determines whether a parameter "is Milestone" is set. The is Milestone parameter is usually set to indicate the last ProtocolEvent object in a major stage of the protocol (such as enrollment, treatment, follow-up), or the first ProtocolEvent object in a major stage of the protocol. It is desirable to show milestone events in a different color and shape. This was the case with the aquamarine ProtocolEvent object 3820 in FIG. 38.

If the current object does have the is Milestone parameter set, then the system creates an exact copy of the object, but of type DisambiguationMilestoneOrTask. The new object is then added to the PresentationSchemaDiagram object being formed. If "is Milestone" is not set, and the object is already of class DisambiguationProtocolEvent (step 3922), then the system adds the object as is to the PresentationSchemaDiagram object being formed. If "is Milestone" is not set, and the current object is directly of class ProtocolEvent, then the system creates an exact copy of the object, but of type DisambiguationProtocolEvent, and adds the new object to the PresentationSchemaDiagram object being formed. Next, in step 3926, the system determines whether there are any more objects to be walked in the selected TemporalSchemaDiagram object. If so, then the system returns to step 3914 for processing the next object.

If in step 3918 the system determines that no disambiguation object is associated with the current ProtocolEvent object, then in step 3928, the system determines whether "is Milestone" is set. If so, then the system creates an exact copy of the current object, but in class DistinguishedMilestoneOrTask, and the system adds the new object to the PresentationSchemaDiagram object being formed. If the current object is of class DisambiguationProtocolEvent (step 3930), then the system creates an exact copy of the current object, but directly in class ProtocolEvent. The system then adds the new object to the PresentationSchemaDiagram object being formed. If "is Milestone" is not set, and the current object is directly of class ProtocolEvent, then the system adds the object as is to the PresentationSchemaDiagram object being formed. The system then proceeds again with step 3926 to determine whether there any more objects to be walked in the selected TemporalSchemaDiagram object.

If in step 3916, the current object was determined to be a TemporalLink object rather than a ProtocolEvent object, then in step 3934, the system determines whether a disambiguation object is associated with the TemporalLink object. Again, whereas a different embodiment might operate differently, in the present embodiment a disambiguation object is considered to be associated with a given TemporalLink object even if it is associated only indirectly. If a disambiguation object is attached to the current TemporalLink object, then in step 3936, the system determines whether the object is already of class DisambiguationTemporalLink. If so, then it adds the object as is to the PresentationSchemaDiagram object being formed. If the current TemporalLink object is directly of class TemporalLink (step 3938), then the system creates an exact copy of the object, but in class DisambiguationTemporalLink. The system then adds the new object to the PresentationSchemaDiagram object being formed. The system next proceeds again with step 3926 to determine whether there any more objects to be walked in the selected TemporalSchemaDiagram object.

If in step 3934 the system determines that there is no disambiguation object attached to the current TemporalLink object, then in step 3940, the system simply adds the current object as is to the PresentationSchemaDiagram object being formed. The system again then continues with step 3926.

If in step 3926 it is determined that there are no more objects to be walked in the selected TemporalSchemaDiagram object, then in step 3942, the problem solver completes by displaying the newly created PresentationSchemaDiagram object.

As mentioned, the process in step 134 (FIG. 1) for creating a desired presentation schema diagram can be performed in a number of different ways. FIG. 39 illustrates one of the ways. In an embodiment in which protocol element objects are created and linked together manually rather than graphically, a Protégé 2000 problem solver might develop a presentation schema diagram by automatically walking from ProtocolEvent object to ProtocolEvent object along the connecting TemporalLink objects, and building up the graphical representation as it proceeds. In another embodiment, a Protégé 2000 problem solver automatically walks the ProtocolEvent objects and the TemporalLink objects, in order to develop a temporal schema diagram, and then a Protégé 2000 problem solver such as that in FIG. 39 is used to develop a presentation schema diagram from the TemporalSchemaDiagram object. Many other variations will be apparent.

In addition to the problem solving tools described elsewhere herein, the system preferably also includes a protocol disambiguation reporter tool which extracts all of the disambiguation comments that have been created for one or more protocols, and presents them in a table format. The tool takes one or more user-selected iCP's as input and gathers all DisambiguationComment objects from all selected iCPs into one group before sorting. In one embodiment, the tool traverses objects in an iCP in accordance with graphical network sequence, such as in accordance with whatever algorithm is used in step 3914 (FIG. 39). In another embodiment, the tool traverses objects in an iCP using an arbitrary sequence internal to the iCP, such as in accordance with an internal list of all objects, or an internal list of only objects of class DisambiguationComment, etc. The sequence of traversal matters little, since the extracted disambiguation comments are typically re-sorted anyway before reporting.

The reporter tool produces either or both of two outputs: (a) a sorted output that is either in a word processor format or which can be converted or imported into a word processor, and (b) a file containing a list of all object instances that have a non-empty disambiguationComments attribute. Output (b) may be superfluous in a system that also includes the tool of FIGS. 1 and 39.

The reporter tool uses a default sort order (highest first) that is primarily by Impact Type and secondarily by the conceptualProtocolSection of attached DocumentReference objects. In another embodiment, the primary and secondary sort criteria are selected by a user. When an item is being sorted by a field that has multiple values, the reporter tool ranks it according to its highest ranking value in the sort order for that field, and does not repeat that finding elsewhere in the output for the other values of that field. Thus each finding appears only once in the report.

The reporter tool outputs one table row for each DisambiguationComment. It assigns a number, in order, for each new row representing a new DisambiguationComment. The reporter tool uses the multiple ProtocolText snippets within the DisambiguationComment's multiple DocumentReferences, along with the DisambiguationComment fields Issue, Potential Impact, and Recommendation to construct a single column called Description within each row. The document references from the pertinent DocumentReference objects are extracted and output in the last column of each row.

FIGS. 40 and 41 illustrate two example rows from a Protocol Disambiguation report table output by the reporter tool. Many other formats will also suffice for different embodiments.

As used herein, a given event or value is "responsive" to a predecessor event or value if the predecessor event or value influenced the given event or value. If there is an intervening step or time period, the given event or value can still be "responsive" to the predecessor event or value. If the intervening step combines more than one event or value, the output of the step is considered "responsive" to each of the event or value inputs. If the given event or value is the same as the predecessor event or value, this is merely a degenerate case in which the given event or value is still considered to be "responsive" to the predecessor event or value. "Dependency" of a given event or value upon another event or value is defined similarly.

The foregoing description of preferred embodiments of the present invention has been provided for the purposes of illustration and description. It is not intended to be exhaustive or to limit the invention to the precise forms disclosed. Obviously, many modifications and variations will be apparent to practitioners skilled in this art. As an example, whereas some of the embodiments described herein are implemented using an object-oriented model, other embodiments can be implemented using a relational database model. In addition, and without limitation, any and all variations described, suggested or incorporated by reference in the Background section of this patent application are specifically incorporated by reference into the description herein of embodiments of the invention. The embodiments described herein were chosen and described in order to best explain the principles of the invention and its practical application, thereby enabling others skilled in the art to understand the invention for various embodiments and with various modifications as are suited to the particular use contemplated. It is intended that the scope of the invention be defined by the following claims and their equivalents.

The invention claimed is:

1. A method for evaluating a clinical trial protocol specification, comprising the steps of:
    encoding into a database, workflow tasks called for in a clinical trial protocol specification not yet in execution, including substeps of writing, into protocol specification objects of said database, specifications of protocol events that said protocol specifies to occur during execution of said protocol, and relationships that said protocol specifies among said protocol events;
    during said step of encoding workflow tasks but not during any of said substeps, identifying an operational uncertainty in which said protocol specification contains at least one of the following deficiencies: said protocol specification fails to specify a particular parameter for use during protocol execution, or said protocol specification specifies such a parameter with less precision than is required by a slot in said database for encoding the parameter, or said protocol specification contains at least two such parameter specifications which are in conflict;
    encoding into said database in association with at least a particular one of said protocol specification objects in said database, before execution of said clinical trial protocol, an indication that said operational uncertainty exists with respect to said particular object; and
    in dependence upon protocol specification objects in said database, before execution of said clinical trial protocol, displaying a graphical-visual representation of said protocol, said graphical-visual representation including a human-perceptible indication that said particular protocol specification object has said operational uncertainty associated therewith.

2. A method according to claim 1, wherein said database is an object-oriented database.

3. A method according to claim 1, wherein said protocol specification objects include protocol event objects describing protocol events, and temporal constraint objects describing temporal constraints among said protocol event objects.

4. A method according to claim 3, wherein said step of displaying comprises the step of displaying each of said protocol specification objects in a color which differs depending on whether an operational uncertainty is associated therewith.

5. A method according to claim 1, wherein said step of displaying comprises the step of displaying each of said protocol specification objects in a color which differs depending on whether an operational uncertainty is associated therewith.

6. A method according to claim 1, wherein said operational uncertainty comprises said protocol specification containing at least two parameter specifications which are in conflict.

7. A method according to claim 1, wherein said operational uncertainty comprises said protocol specification specifying a parameter with less precision than is required by a slot in said database.

8. A method according to claim 1, wherein said operational uncertainty comprises an omitted parameter in said protocol specification.

9. A method according to claim 1, wherein said operational uncertainty concerns a temporal constraint among at least two of said protocol events.

10. A set of at least one computer readable medium, said set carrying a machine readable database which includes protocol specification objects describing protocol events that a protocol specification specifies to occur during execution of said protocol, and relationships among said protocol events,
    said database further including a disambiguation comment object which identifies an operational uncertainty in which said protocol specification contains at least one of the following deficiencies: said protocol specification fails to specify a particular parameter for use during protocol execution, or said protocol specification specifies such a parameter with less precision than is required by a slot in said database for encoding the parameter, or said protocol specification contains at least two such parameter specifications which are in conflict, said disambiguation comment object being associated with at least a particular one of said objects in said database.

11. A medium according to claim 10, wherein said database is an object-oriented database.

12. A medium according to claim 10, wherein said protocol specification objects include protocol event objects describing protocol events, and temporal constraint objects describing temporal constraints among said protocol event objects.

13. A medium according to claim 12, wherein said disambiguation comment object is associated with one of said protocol event objects.

14. A medium according to claim 12, wherein said disambiguation comment object is associated with a particular one of said temporal constraint objects.

15. A medium according to claim 14, wherein said operational uncertainty concerns the amount of time allowed to elapse between two protocol events identified by said particular temporal constraint object.

16. A medium according to claim 12, wherein said protocol specification objects further include workflow task objects.

17. A medium according to claim 16, wherein each of said workflow task objects is associated with at least one of said protocol event objects.

18. A medium according to claim 16, wherein said disambiguation comment object is associated with one of said workflow task objects.

19. A medium according to claim 10, wherein said operational uncertainty comprises said protocol specification containing at least two parameter specifications which are in conflict.

20. A medium according to claim 10, wherein said operational uncertainty comprises said protocol specification specifying a parameter with less precision than is required by a slot in said database.

21. A medium according to claim 10, wherein said operational uncertainty comprises an omitted parameter in said protocol specification.

22. A medium according to claim 10, wherein said operational uncertainty concerns the amount of time allowed to elapse between two of said protocol events.

23. A method for evaluating a clinical trial protocol specification, comprising the steps of:
  encoding into a database, workflow tasks called for in a clinical trial protocol specification not yet in execution, including substeps of writing, into protocol specification objects of said database, specifications of protocol events that the protocol specifies to occur during execution of the protocol, and relationships that the protocol specifies among said protocol events;
  during said step of encoding workflow tasks but not during any of said substeps, identifying an operational uncertainty in which said protocol specification contains at least one of the following deficiencies: said protocol specification fails to specify a parameter for use during protocol execution, or said protocol specification specifies such a parameter with less precision than is required by a slot in said database for encoding the parameter, or said protocol specification contains at least two such parameter specifications which are in conflict;
  encoding into said database in association with at least a particular one of said protocol specification objects in said database, before execution of said clinical trial protocol, an indication that said operational uncertainty exists with respect to the particular protocol specification object; and
  in dependence upon objects in said database, before execution of said clinical trial protocol, outputting a report setting forth the operational uncertainties identified in said protocol and encoded into said database.

24. A method according to claim 23, further comprising the steps of:
  encoding into a protocol disambiguation object said indication that said operational uncertainty exists; and
  associating said protocol disambiguation object with said particular protocol specification objects in said database.

25. A method according to claim 24, wherein said protocol specification objects include protocol event objects describing protocol events, and temporal constraint objects describing temporal constraints among protocol events described in said protocol event objects,
  and wherein said step of associating comprises the step of associating said protocol disambiguation object with one of said protocol event objects or one of said temporal constraint objects in said database.

26. A method according to claim 23, wherein said database is an object-oriented database.

27. A method according to claim 23, further comprising the step, prior to said step of outputting, of sorting a list of said operational uncertainties identified in said protocol and encoded into said database.

28. A method according to claim 23, wherein said step of outputting comprises the step of outputting in tabular form the operational uncertainties identified in said protocol and encoded into said database.

29. A method according to claim 23, wherein said operational uncertainty comprises said protocol specification containing at least two parameter specifications which are in conflict.

30. A method according to claim 23, wherein said operational uncertainty comprises said protocol specification specifying a parameter with less precision than is required by a slot in said database.

31. A method according to claim 23, wherein said operational uncertainty comprises an omitted parameter in said protocol specification.

32. A method according to claim 23, wherein said operational uncertainty concerns a temporal constraint among at least two of said protocol events specification.

* * * * *